US008088902B2

(12) United States Patent
Pfeffer et al.

(10) Patent No.: US 8,088,902 B2
(45) Date of Patent: Jan. 3, 2012

(54) DNA VIRUS MICRORNA AND METHODS FOR INHIBITING SAME

(75) Inventors: Sebastien Pfeffer, New York, NY (US); Thomas Tuschl, New York, NY (US)

(73) Assignee: The Rockefeller University, New York, NY (US)

(*) Notice: Subject to any disclaimer, the term of this patent is extended or adjusted under 35 U.S.C. 154(b) by 156 days.

(21) Appl. No.: 10/968,821

(22) Filed: Oct. 19, 2004

(65) Prior Publication Data

US 2005/0222067 A1      Oct. 6, 2005

Related U.S. Application Data

(63) Continuation-in-part of application No. 10/925,363, filed on Aug. 24, 2004, now abandoned, which is a continuation-in-part of application No. 10/819,098, filed on Apr. 5, 2004, now Pat. No. 7,416,842.

(51) Int. Cl.
C07H 23/00           (2006.01)

(52) U.S. Cl. .................. 536/23.1; 536/23.72; 435/5

(58) Field of Classification Search ........................ None
See application file for complete search history.

(56) References Cited

U.S. PATENT DOCUMENTS

| | | | | |
|---|---|---|---|---|
| 5,721,354 | A * | 2/1998 | Spaete et al. | 536/23.72 |
| 6,692,954 | B1 * | 2/2004 | Ghazal et al. | 435/320.1 |
| 7,217,807 | B2 | 5/2007 | Bentwich | |
| 7,250,289 | B2 * | 7/2007 | Zhou | 435/287.2 |
| 7,314,750 | B2 * | 1/2008 | Zhou | 435/287.2 |
| 7,341,835 | B2 * | 3/2008 | Blume et al. | 435/6 |
| 7,365,058 | B2 | 4/2008 | Stoffel et al. | |
| 2003/0060611 | A1 * | 3/2003 | Blatt et al. | 536/23.1 |
| 2003/0082596 | A1 * | 5/2003 | Mittmann | 435/6 |
| 2003/0108923 | A1 | 6/2003 | Tuschl et al. | |
| 2006/0166910 | A1 | 7/2006 | Tuschl et al. | |
| 2006/0257851 | A1 | 11/2006 | Bentwich | |
| 2007/0039072 | A1 | 2/2007 | Khvorova et al. | |
| 2007/0042381 | A1 | 2/2007 | Bentwich et al. | |
| 2007/0287179 | A1 | 12/2007 | Tuschl et al. | |
| 2008/0097092 | A1 * | 4/2008 | Khvorova et al. | 536/24.5 |
| 2008/0114162 | A1 | 5/2008 | Khvorova et al. | |
| 2008/0188428 | A1 | 8/2008 | Bentwich | |
| 2008/0318210 | A1 * | 12/2008 | Bentwich | 435/6 |
| 2009/0275729 | A1 | 11/2009 | Stoffel et al. | |

FOREIGN PATENT DOCUMENTS

| | | | |
|---|---|---|---|
| WO | WO 99/19732 | * | 4/1999 |
| WO | WO 01/59103 A2 | * | 8/2001 |
| WO | WO2004/044123 A2 | | 5/2004 |
| WO | WO/2004/048511 | * | 6/2004 |
| WO | WO2004/048511 A2 | | 6/2004 |
| WO | WO2005013901 A2 | | 2/2005 |
| WO | WO2005079397 A2 | | 9/2005 |
| WO | WO2006033020 A2 | | 3/2006 |
| WO | WO2006047454 A2 | | 5/2006 |
| WO | WO2006119266 A2 | | 11/2006 |

OTHER PUBLICATIONS

AC146999, Murphy et al. Oct. 31, 2003, p. 1-67.*
Murphy et al. PNAS, vol. 100, p. 14976-14981.*
Pfeffer et al. Nature Methods, 2005, vol. 2, p. 269-276.*
Amarzguioui, Mohammed, et al., "Tolerance for mutations and chemical modifications in a siRNA", Nucleic Acids Research 2003, 31(2):589-595.
Bartel, David P., "MicroRNAs: Genomics, Biogenesis, Mechanism, and Function", Cell 2004, 116:281-297.
Beigelman, Leonid, et al., "Chemical Modification of Hammerhead Ribozymes", The Journal of Biological Chemistry 1995, 270(43):25702-25708.
Elbashir, Sayda M., et al., "Duplexes of 21-nucleotide RNAs mediate RNA interference in cultured mammalian cells", Nature 2001, 411:494-498.
Holen, Torgeir, et al., "Positional effects of short interfering RNAs targeting the human coagulation trigger Tissue Factor", Nucleic Acids Research 2002, 30(8):1757-1766.
Holen, Torgeir, et al., "Similar behaviour of single-strand and double-strand siRNAs suggests they act through a common RNAi pathway", Nucleic Acids Research 2003, 31(9):2401-2407.
Howard, Ken, "Unlocking the money-making potential of RNAi", Nature Biotechnology 2003, 21(12):1441-1446.
Kurreck, Jens, "Antisense technologies Improvement through novel chemical modifications", Eur. J. Biochem. 2003, 270:1628-1644.
Meister, Gunter, et al., "Sequence-specific inhibition of microRNA- and siRNA-induced RNA silencing", RNA 2004, 10:544-550.
Nelson, Peter, et al., "The microRNA world: small is mighty", TRENDS in Biochemical Sciences 2003, 28(10):534-540.
Berezikov et al., "Phylogenetic Shadowing and Computational Identification of Human MicroRNA Genes", Cell, vol. 120, pp. 21-24 (2005).
Seitz, et al., "A Large Imprinted MicroRNA Gene Cluster at the Mouse Elkl-Gt12 Domain", Genome Research, pp 2. 1-8 (2004).
Xie et al., "Systematic Discovery of Regulatory Motifs in Human Promoters and 3 UTR's by Comparison of Several Mammals", Nature, pp. 1-8 (2005).
U.S. Appl. No. 10/604,945, filed Aug. 27, 2003, Bentwich et al.
U.S. Appl. No.10/604,984, filed Aug. 29, 2003, Bentwich et al.
U.S. Appl. No. 10/708,952, filed Apr. 2, 2004, Bentwich et al.
Analysis and accompanying remarks by Rosetta Genomics of the sequences presented in Table A2 of the specification of the instant application (Jun. 28, 2007).
Table of information provided by Rosetta regarding the applications submitted in IDS dated Jul. 12, 2007 (Jun. 28, 2007).
Analysis by Rosetta of the sequences of Table A2 compared to those disclosed in Rosetta's patent applications (Jun. 28, 2007).

(Continued)

Primary Examiner — Agnieszka Boesen
(74) Attorney, Agent, or Firm — Hoffman & Baron, LLP

(57) ABSTRACT

The invention relates to isolated nucleic acid molecules comprising the sequence of a human cytomegalovirus microRNA. In another embodiment, the invention relates to single stranded DNA virus microRNA molecules comprising the sequence of a human cytomegalovirus microRNA. The invention also relates to the anti-DNA virus microRNA molecules.

4 Claims, 8 Drawing Sheets

OTHER PUBLICATIONS

Avavin et al., "The Small RNA Profile During Drosophila Melanogaster Development", Developmental Cell, vol. 5, p. 337-350 (2003).

Database EMBL (Online), *Homo sapiens* Genomic Sequence Surrounding Notl site, clone NR3-B07C, XP002451881 retrieved from EBI accession No. EMBL: AJ332626: 21/22 residues match SEQ ID No. 1; Oct. 2001, abstract.

Liang et al., "Inhibitor RNA Blocks the Protein Translation Mediated by Hepatitis C Virus Internal Ribosome Entry Site in Vivo", World J. Gastroenterol, 10(5), p. 664-667 (2004).

Database EMBL (Online), NISC_js08a05.w1 Soares NMBP1 *Mus musculus* cDNA clone Image: 4314537 5', mRNA sequence, XP002451882 retrieved from EBI accession No. EMBL: CB057718; 22/22 residues match SEQ ID No. 3; Jan. 2003, abstract.

Database EMBL (Online), CH4#001_G02T7 Canine Heart Normalized CDNA Library in pBluescript *Canis familaris* cDNA clone CH4#001_G02 5', mRNA sequence. XP002451883 retrieved from EBI accession No. EMBL: BU751380: 22/22 residues match SEQ ID No. 4; Oct. 2002, abstract.

Taliansky et al., "An Umbraviral Protein, Involved in Long-Distance RNA Movement, Binds Viral RNA and Forms Unique, Protective Ribonucleoprotin Complexes", Journal of Virology, vol. 77, No. 5, p. 3031-3040 (2003).

Paddison et al., "Short Hairpin RNAs (shRNAs) Induce Sequence-Specific Silencing in Mammalian Cells", Genes & Development, 16:948-958 (2002).

Wiebusch et al., "Inhibition of Human Cytomegalovirus Replication by Small Interfering RNAs", Journal of General Virology, 85, p. 179-184 (2004).

Vanitharani et al., "Short Interfering RNA-Mediated Interference of Gene Expression and Viral DNA Accumulation in Cultured Plant Cells", PNAS, vol. 100, No. 16, p. 9632-9636 (2003).

Pfitzner et al., "Isolation and Characterization of cDNA Clones Corresponding to Transcripts from the BamHl H and F Regions of the Epstein-Barr Virus Genome", Journal of Virology, vol. 61, No. 9, p. 2902-2909 (1987).

Pfeffer et al., "Indentification of Virus-Encoded microRNAs", Science, vol. 304, p. 734-736 (2004).

Pfeffer et al., "Identification of microRNAs of the Herpesvirus Family", Nature Methods, Published Online DOI:10.1038/NMETH746, p. 1-8.

Zeng, et al., "MicroRNAs and Small Interfering RNAs Can Inhibit mRNA Expression by Similar Mechanisms", PNAS, vol. 100, No. 17, p. 9779-9784 (2003).

Boutla et al., "Developmental Defects by Antisense-Mediated Inactivation of Micr-RNAs 2 and 13 in *Drosophila* and the Identification of Putative Target Genes", Nucleic Acids Research, vol. 31, No. 17, pp. 4973-4980 (2003).

Kawasaki et al., "Hes1 is a Target of MicroRNA-23 During Retinoic-Acid-Induced Neutonal Differentiation of NT2 Cells", Nature, vol. 423, No. 6942, pp. 838-842 (2003).

Mourelatos et al., "MiRNPs: A Novel Class of Ribonucleoproteins Containing Numerous microRNAs", Genes and Development, vol. 16, No. 6, pp. 720-728 (2002).

Hutvagner et al., "Sequence-Specific Inhibition of Small HRN function", PLOS Biology, Public Library of Science, vol. 2, No. 4, pp. 465-475 (2004).

Database EMBL (Online), "*Homo sapiens* MicroRNAs hsa-RG-33, Complete Sequence", XP002598630 retrieved from EBI Accession No. EMBL:AY785943, Nov. 2004.

Dostie et al., "Numerous MicroRNPs in Neuronal Cells Containing Novel MicroRNAs", RNA, Cold Spring Habor Laboratory Press, vol. 9, No. 2, pp. 180-186 (Feb. 2003).

Cupido, Marinus, Supplementary European Search Report for corresponding European Application No. EP06752071, Aug. 31, 2010, pp. 1-10.

\* cited by examiner

Figure 1

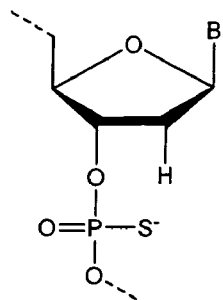

Phosphorothioate DNA Unit
(PS)
Structure 1

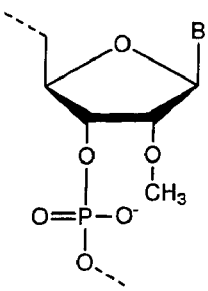

2'-O-methyl RNA unit
(OMe)
Structure 3

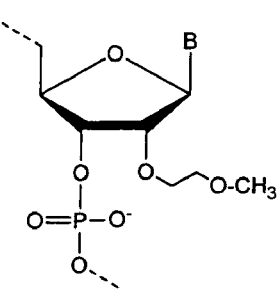

2'-O-methoxy-ethyl RNA unit
(MOE)
Structure 4

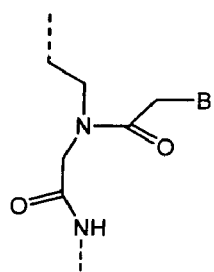

Peptide nucleic acid unit
(PNA)
Structure 6

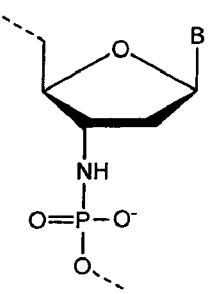

N3'-P5' Phosphoroamidate DNA unit
(NP)
Structure 2

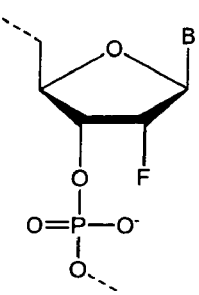

2'-fluoro-ribo nucleic acid unit
(FANA)
Structure 7

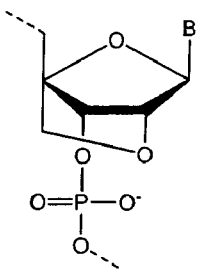

Locked nucleic acid unit
(LNA)
Structure 5

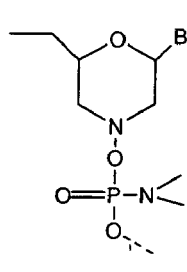

Morpholino phosphoroamidate
nucleic acid unit
(MF)
Structure 8

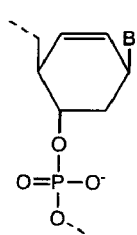

Cyclohexane nucleic acid unit
(CeNA)
Structure 10

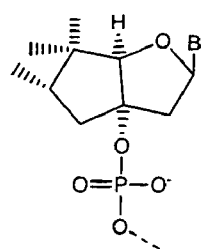

Tricyclonucleic acid unit
Structure 9

Figures 2A and B
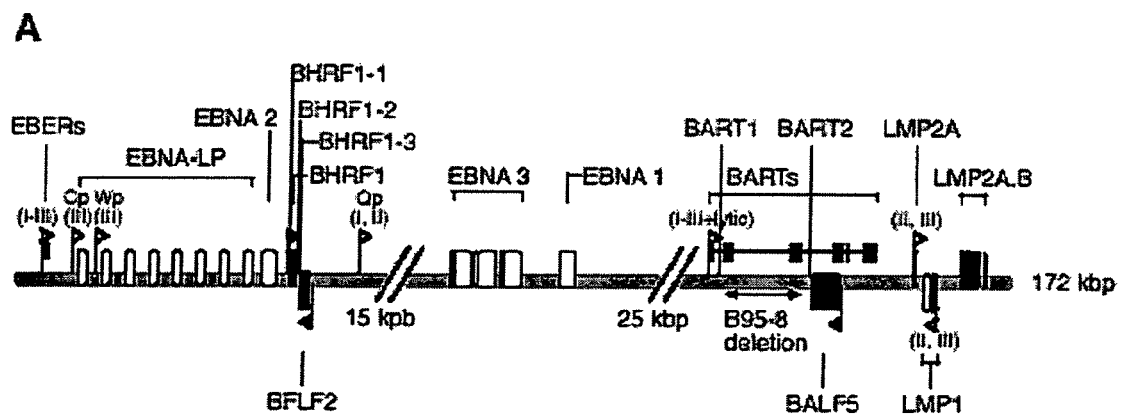
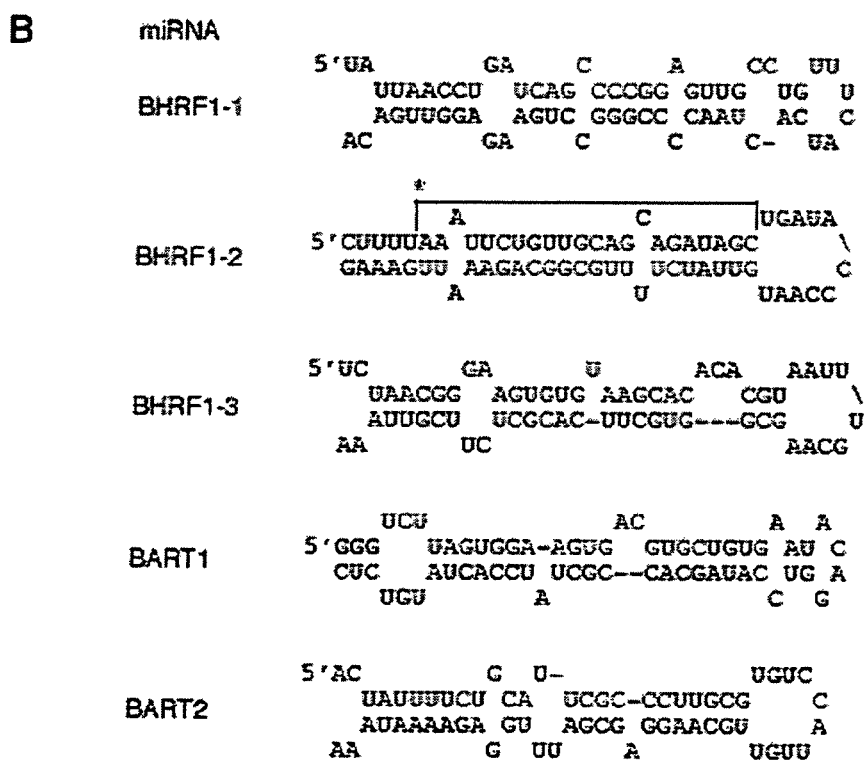

Figures 2C and D
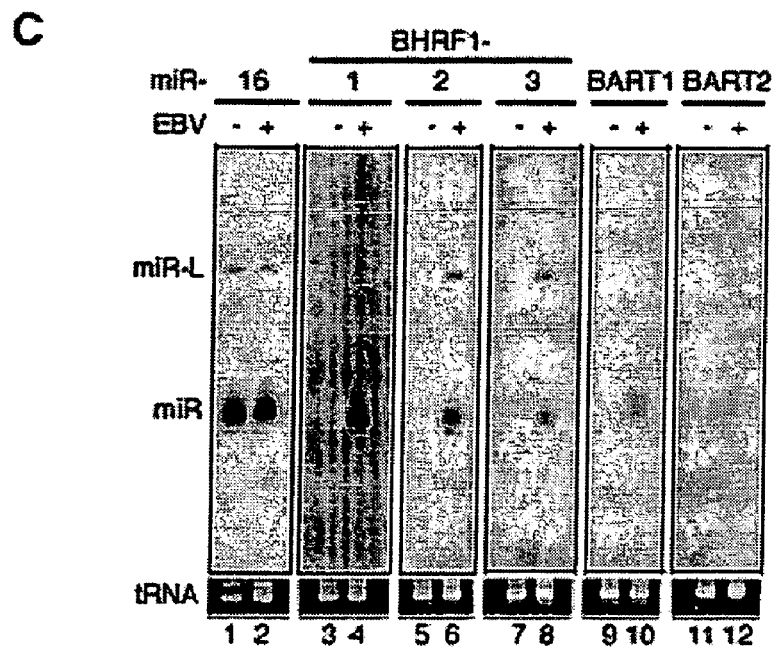
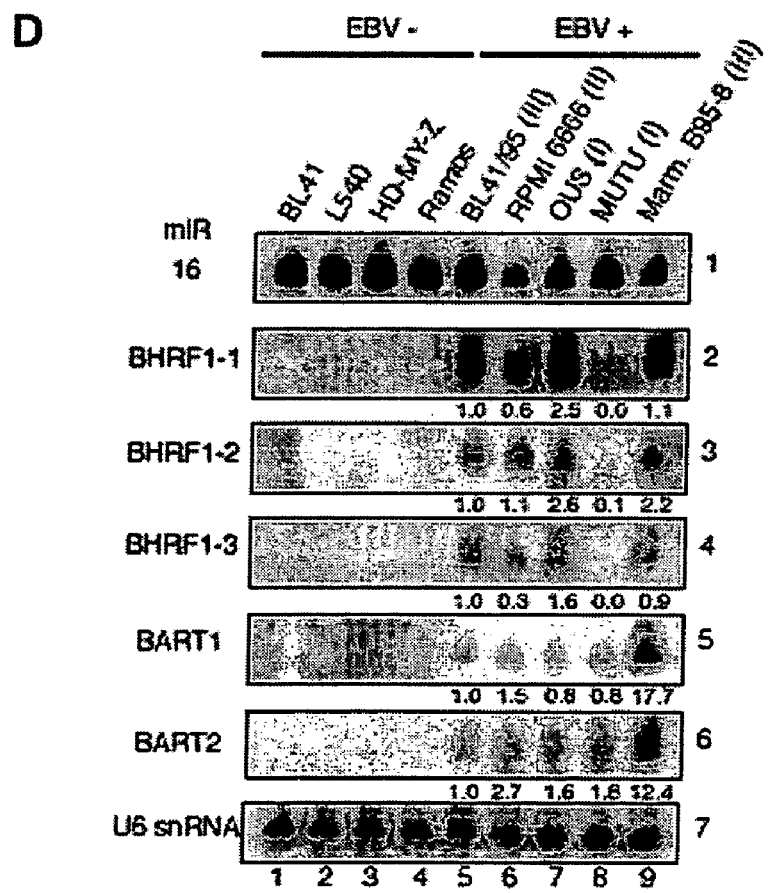

Figure 4B microRNA

K1
```
5'    AG       C     C   CAC      UGU
    CUGG  GCUUGGGG GAUA CAC   UCGUU   C
    GACC  UGAGCCCC CUGU GUG   AGCGG   U
       GG         C   U   AUU      UUG
```

K2
```
5'     C    C          A    C   CGU
    GGGU UAC CAGCUGCGUA ACCC GCUG   A
    CCCA AUG GUCGACGCAU UGGG CGAC   A
       A    C          A    U   ACA
```

K10
```
5'    CA   C    CUAA    CC   UUUG  UG
    CGCG  CUC  CUCA    CGCC  GCU    UC  \
    GCGC  GAG  GAGU    GCGG  CGA    AG  U
       AC    A    CAGC    AU    CGA-  GU
```

K8
```
5' G  U        C   ACG       U   CU-   U
   CGU GAGCGCCA CGG   GGGAUU AUG   GUA  \
   GCA CUCGCGGU GUU   CCCUAG UAC   CAU  C
    G  -        C   GUA       -   CAU   U
```

K9
```
5'  U   U     C    A    UCU    CGGUG
   CGC UUGG CACAG UUAA CAUU   AGGG   \
   GCG AGCC GUGUC GAUU GUAA   UCCU    U
    U   U    C    C    U--    AGUAU
```

K3
```
5'    UC     A  U  U-       GG
    CUUG CAGCAGC CC AA  CCAUCGC   U
    GAGC GUUGUCG GG UU  GGUAGCG   C
       GA          -  C  UU     GG
```

K4
```
5' U  UA    -  C  U   GC     G  U  AC
   GACC GGUA GU CC GGU  CCUAAG G CU  A
   CUGG CCGU CA GG CCG  GGAUUC C GA  U
    A   --    U  A  U   UA     A  -  AC
```

K5
```
5'    C     AA   G    C    GG--   UU
    AUAA UAGCUA  CC CAGUA UCUA    GCA  C
    UAUU GUCGAU  GG GUCAU AGAU    UGU  A
       A     CC    A    A    ACAU    UU
```

K6
```
5' CUA        AG  G  A  ---     GUG
   GG  UCACAUUCUG GAC GC GC   GACGU   \
   CC  AGUGUAAGAC CUG CG UG   CUGCA   U
    AC-         A-   G  C  CAA    AUC
```

K7
```
5'  ---  A      U       AA     UACAU
    GCGA  UU CAGGAAAC GGGUGU  GCUG    \
    UGCU  AA GUCCUUUG UCCACG  CGGC    A
       CCC  C         -       A-  CCCUA
```

Figure 6
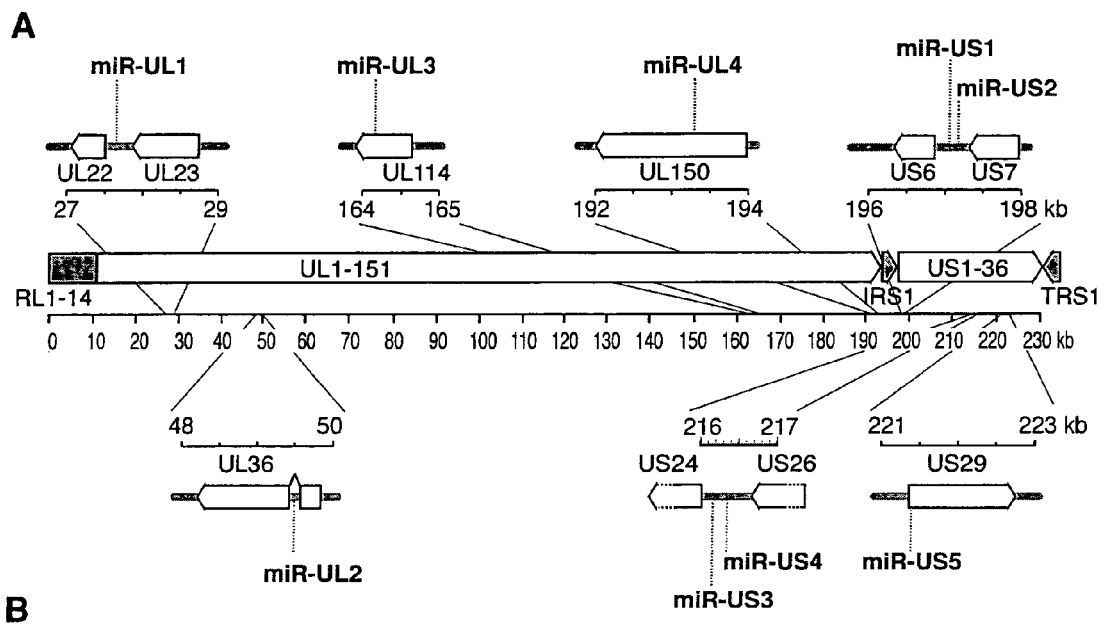
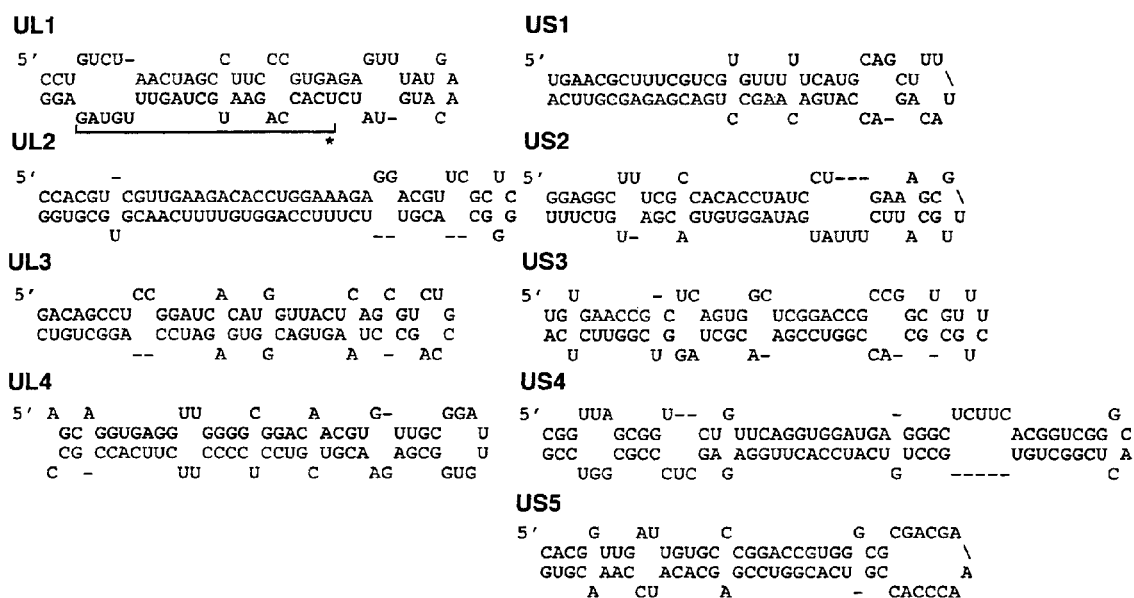

SEQUENCE LISTING

<160> NUMBER OF SEQ ID NOS: 105

<210> SEQ ID NO 1
<211> LENGTH: 22
<212> TYPE: RNA
<213> ORGANISM: Epstein Bar Virus

<400> SEQUENCE: 1
uaaccugauc agccccggag uu                                              22

<210> SEQ ID NO 2
<211> LENGTH: 23
<212> TYPE: RNA
<213> ORGANISM: Epstein Bar Virus

<400> SEQUENCE: 2

```
uaucuuuugc ggcagaaauu gaa                                           23

<210> SEQ ID NO 3
<211> LENGTH: 23
<212> TYPE: RNA
<213> ORGANISM: Epstein Bar Virus

<400> SEQUENCE: 3
uaacgggaag uguguaagca cac                                           23

<210> SEQ ID NO 4
<211> LENGTH: 21
<212> TYPE: RNA
<213> ORGANISM: Epstein Bar Virus

<400> SEQUENCE: 4
ucuuagugga agugacgugc u                                             21

<210> SEQ ID NO 5
<211> LENGTH: 22
<212> TYPE: RNA
<213> ORGANISM: Epstein Bar Virus

<400> SEQUENCE: 5
uauuuucugc auucgcccuu gc                                            22

<210> SEQ ID NO 6
<211> LENGTH: 66
<212> TYPE: RNA
<213> ORGANISM: Epstein Bar Virus

<400> SEQUENCE: 6
uauuaaccug aucagccccg gaguugccug uuucaucacu aaccccgggc cugaagaggu   60
ugacaa                                                              66

<210> SEQ ID NO 7
<211> LENGTH: 65
<212> TYPE: RNA
<213> ORGANISM: Epstein Bar Virus

<400> SEQUENCE: 7
cuuuuaaauu cuguugcagc agauagcuga uacccaaugu uaucuuuugc ggcagaaauu   60
gaaag                                                               65

<210> SEQ ID NO 8
<211> LENGTH: 65
<212> TYPE: RNA
<213> ORGANISM: Epstein Bar Virus

<400> SEQUENCE: 8
ucuaacggga aguguguaag cacacacgua auuugcaagc ggugcuucac gcucuucguu   60
aaaau                                                               65

<210> SEQ ID NO 9
<211> LENGTH: 70
<212> TYPE: RNA
<213> ORGANISM: Epstein Bar Virus

<400> SEQUENCE: 9
cggggucuua guggaaguga cgugcuguga auacaggucc auagcaccgc uauccacuau   60
gucucgcccg                                                          70
```

-continued

<210> SEQ ID NO 10
<211> LENGTH: 62
<212> TYPE: RNA
<213> ORGANISM: Epstein Bar Virus

<400> SEQUENCE: 10
acuauuuucu gcauucgccc uugcgugucc auuguugcaa ggagcgauuu ggagaaaaua    60
aa    62

<210> SEQ ID NO 11
<211> LENGTH: 22
<212> TYPE: RNA
<213> ORGANISM: Epstein Bar Virus

<400> SEQUENCE: 11
aacuccgggg cugaucaggu ua    22

<210> SEQ ID NO 12
<211> LENGTH: 23
<212> TYPE: RNA
<213> ORGANISM: Epstein Bar Virus

<400> SEQUENCE: 12
uucaauuucu gccgcaaaag aua    23

<210> SEQ ID NO 13
<211> LENGTH: 23
<212> TYPE: RNA
<213> ORGANISM: Epstein Bar Virus

<400> SEQUENCE: 13
gugugcuuac acacuucccg uua    23

<210> SEQ ID NO 14
<211> LENGTH: 21
<212> TYPE: RNA
<213> ORGANISM: Epstein Bar Virus

<400> SEQUENCE: 14
agcacgucac uuccacuaag a    21

<210> SEQ ID NO 15
<211> LENGTH: 22
<212> TYPE: RNA
<213> ORGANISM: Epstein Bar Virus

<400> SEQUENCE: 15
gcaagggcga augcagaaaa ua    22

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16 gcagggggcca tgctaatctt ctctgtatcg    30

<210> SEQ ID NO 17
<211> LENGTH: 22
<212> TYPE: RNA
<213> ORGANISM: Epstein Bar Virus

```
<400> SEQUENCE: 17
aaauucuguu gcagcagaua gc                                              22

<210> SEQ ID NO 18
<211> LENGTH: 22
<212> TYPE: RNA
<213> ORGANISM: Kaposi's sarcoma-associated herpesvirus

<400> SEQUENCE: 18
uaguguuguc cccccgagug gc                                              22

<210> SEQ ID NO 19
<211> LENGTH: 22
<212> TYPE: RNA
<213> ORGANISM: Kaposi's sarcoma-associated herpesvirus

<400> SEQUENCE: 19
ugguguuguc cccccgagug gc                                              22

<210> SEQ ID NO 20
<211> LENGTH: 22
<212> TYPE: RNA
<213> ORGANISM: Kaposi's sarcoma-associated herpesvirus

<400> SEQUENCE: 20
acccagcugc guaaaccccg cu                                              22

<210> SEQ ID NO 21
<211> LENGTH: 22
<212> TYPE: RNA
<213> ORGANISM: Kaposi's sarcoma-associated herpesvirus

<400> SEQUENCE: 21
cuggguauac gcagcugcgu aa                                              22

<210> SEQ ID NO 22
<211> LENGTH: 22
<212> TYPE: RNA
<213> ORGANISM: Kaposi's sarcoma-associated herpesvirus

<400> SEQUENCE: 22
ccagcagcac cuaauccauc gg                                              22

<210> SEQ ID NO 23
<211> LENGTH: 22
<212> TYPE: RNA
<213> ORGANISM: Kaposi's sarcoma-associated herpesvirus

<400> SEQUENCE: 23
ugaugguuuu cgggcuguug ag                                              22

<210> SEQ ID NO 24
<211> LENGTH: 22
<212> TYPE: RNA
<213> ORGANISM: Kaposi's sarcoma-associated herpesvirus

<400> SEQUENCE: 24
uaggaugccu ggaacuugcc gg                                              22

<210> SEQ ID NO 25
<211> LENGTH: 22
<212> TYPE: RNA
<213> ORGANISM: Kaposi's sarcoma-associated herpesvirus
```

```
<400> SEQUENCE: 25
agcuaaaccg caguacucua gg                                              22

<210> SEQ ID NO 26
<211> LENGTH: 22
<212> TYPE: RNA
<213> ORGANISM: Kaposi's sarcoma-associated herpesvirus

<400> SEQUENCE: 26
uagaauacug aggccuagcu ga                                              22

<210> SEQ ID NO 27
<211> LENGTH: 22
<212> TYPE: RNA
<213> ORGANISM: Kaposi's sarcoma-associated herpesvirus

<400> SEQUENCE: 27
ucacauucug aggacggcag cg                                              22

<210> SEQ ID NO 28
<211> LENGTH: 22
<212> TYPE: RNA
<213> ORGANISM: Kaposi's sarcoma-associated herpesvirus

<400> SEQUENCE: 28
ucgcggucac agaaugugac ac                                              22

<210> SEQ ID NO 29
<211> LENGTH: 22
<212> TYPE: RNA
<213> ORGANISM: Kaposi's sarcoma-associated herpesvirus

<400> SEQUENCE: 29
auuacaggaa acugggugua ag                                              22

<210> SEQ ID NO 30
<211> LENGTH: 22
<212> TYPE: RNA
<213> ORGANISM: Kaposi's sarcoma-associated herpesvirus

<400> SEQUENCE: 30
ugaucccaug uugcuggcgc uc                                              22

<210> SEQ ID NO 31
<211> LENGTH: 22
<212> TYPE: RNA
<213> ORGANISM: Kaposi's sarcoma-associated herpesvirus

<400> SEQUENCE: 31
uuaaugcuua gccuguqucc ga                                              22

<210> SEQ ID NO 32
<211> LENGTH: 22
<212> TYPE: RNA
<213> ORGANISM: Kaposi's sarcoma-associated herpesvirus

<400> SEQUENCE: 32
uaggcgcgac ugagagagca cg                                              22

<210> SEQ ID NO 33
<211> LENGTH: 70
<212> TYPE: RNA
<213> ORGANISM: Kaposi's sarcoma-associated herpesvirus
```

<400> SEQUENCE: 33
cuggaggcuu ggggcgauac caccacucgu uugucuguug gcgauuagug uugcccccc       60 gaguggccag                                                             70

<210> SEQ ID NO 34
<211> LENGTH: 70
<212> TYPE: RNA
<213> ORGANISM: Kaposi's sarcoma-associated herpesvirus

<400> SEQUENCE: 34
cuggaggcuu ggggcgauac caccacucgu uugucuguug gcgauuggug uugcccccc       60 gaguggccag                                                             70

<210> SEQ ID NO 35
<211> LENGTH: 66
<212> TYPE: RNA
<213> ORGANISM: Kaposi's sarcoma-associated herpesvirus

<400> SEQUENCE: 35 ggucuaccc agcugcguaa accccgcugc guaaacacag cuggguauac gcagcugcgu       60
aaaccc                                                                 66

<210> SEQ ID NO 36
<211> LENGTH: 65
<212> TYPE: RNA
<213> ORGANISM: Kaposi's sarcoma-associated herpesvirus

<400> SEQUENCE: 36
ggucuaccca gcugcguaaa ccccgcugcg uaaacacagc uggguauacg cagcugcgua       60
aaccc                                                                  65

<210> SEQ ID NO 37
<211> LENGTH: 62
<212> TYPE: RNA
<213> ORGANISM: Kaposi's sarcoma-associated herpesvirus

<400> SEQUENCE: 37
cuuguccagc agcaccuaau ccaucggcgg ucgggcugau gguuuucggg cuguugagcg       60
ag                                                                     62

<210> SEQ ID NO 38
<211> LENGTH: 62
<212> TYPE: RNA
<213> ORGANISM: Kaposi's sarcoma-associated herpesvirus

<400> SEQUENCE: 38
cuuguccagc agcaccuaau ccaucggcgg ucgggcugau gguuuucggg cuguugagcg       60
ag                                                                     62

<210> SEQ ID NO 39
<211> LENGTH: 70
<212> TYPE: RNA
<213> ORGANISM: Kaposi's sarcoma-associated herpesvirus

<400> SEQUENCE: 39
ugaccuaggu agucccuggu gcccuaaggg ucuacaucaa gcacuuagga ugccggaac       60 uugccgguca                                                             70

<210> SEQ ID NO 40

```
<211> LENGTH: 70
<212> TYPE: RNA
<213> ORGANISM: Kaposi's sarcoma-associated herpesvirus

<400> SEQUENCE: 40
auaacuagcu aaaccgcagu acucuagggc auucauuugu acauagaau acugaggccu      60 agcugauuau                                                            70

<210> SEQ ID NO 41
<211> LENGTH: 70
<212> TYPE: RNA
<213> ORGANISM: Kaposi's sarcoma-associated herpesvirus

<400> SEQUENCE: 41
auaacuagcu aaaccgcagu acucuagggc auucauuugu acauagaau acugaggccu      60 agcugauuau                                                            70

<210> SEQ ID NO 42
<211> LENGTH: 70
<212> TYPE: RNA
<213> ORGANISM: Kaposi's sarcoma-associated herpesvirus

<400> SEQUENCE: 42
ggcuaucaca uucugaggac ggcagcgacg ugugcuaac gucaacgucg cggucacaga       60
augugacacc                                                            70

<210> SEQ ID NO 43
<211> LENGTH: 70
<212> TYPE: RNA
<213> ORGANISM: Kaposi's sarcoma-associated herpesvirus

<400> SEQUENCE: 43
ggcuaucaca uucugaggac ggcagcgacg ugugcuaac gucaacgucg cggucacaga       60
augugacacc                                                            70

<210> SEQ ID NO 44
<211> LENGTH: 67
<212> TYPE: RNA
<213> ORGANISM: Kaposi's sarcoma-associated herpesvirus

<400> SEQUENCE: 44
ggauuacagg aaacuggug uaagcuguac auaauccccg gcagcaccug uuuccugcaa       60
cccucgu                                                               67

<210> SEQ ID NO 45
<211> LENGTH: 72
<212> TYPE: RNA
<213> ORGANISM: Kaposi's sarcoma-associated herpesvirus

<400> SEQUENCE: 45
gcguugagcg ccaccggacg gggauuuaug cuguaucuua cuaccaugau cccauguugc      60
uggcgcucac gg                                                         72

<210> SEQ ID NO 46
<211> LENGTH: 71
<212> TYPE: RNA
<213> ORGANISM: Kaposi's sarcoma-associated herpesvirus

<400> SEQUENCE: 46
cgcuuggguc acagcuuaaa cauuucuagg gcgguguuau gauccuuaau gcuuagccug      60
```

```
uguccgaugc g                                                            71

<210> SEQ ID NO 47
<211> LENGTH: 70
<212> TYPE: RNA
<213> ORGANISM: Kaposi's sarcoma-associated herpesvirus

<400> SEQUENCE: 47
cgcgcacucc cucacuaacg ccccgcuuuu gucuguugga agcagcuagg cgcgacugag       60
agagcacgcg                                                              70

<210> SEQ ID NO 48
<211> LENGTH: 22
<212> TYPE: RNA
<213> ORGANISM: Kaposi's sarcoma-associated herpesvirus

<400> SEQUENCE: 48
gccacucggg gggacaacac ua                                                22

<210> SEQ ID NO 49
<211> LENGTH: 22
<212> TYPE: RNA
<213> ORGANISM: Kaposi's sarcoma associated herpesvirus

<400> SEQUENCE: 49
gccacucggg gggacaacac ca                                                22

<210> SEQ ID NO 50
<211> LENGTH: 22
<212> TYPE: RNA
<213> ORGANISM: Kaposi's sarcoma associated herpesvirus

<400> SEQUENCE: 50
agcgggguuu acgcagcugg gu                                                22

<210> SEQ ID NO 51
<211> LENGTH: 22
<212> TYPE: RNA
<213> ORGANISM: Kaposi's sarcoma associated herpesvirus

<400> SEQUENCE: 51
uuacgcagcu gcguauaccc ag                                                22

<210> SEQ ID NO 52
<211> LENGTH: 22
<212> TYPE: RNA
<213> ORGANISM: Kaposi's sarcoma associated herpesvirus

<400> SEQUENCE: 52
ccgauggauu aggugcugcu gg                                                22

<210> SEQ ID NO 53
<211> LENGTH: 22
<212> TYPE: RNA
<213> ORGANISM: Kaposi's sarcoma associated herpesvirus

<400> SEQUENCE: 53
cucaacagcc cgaaaaccau ca                                                22

<210> SEQ ID NO 54
<211> LENGTH: 22
<212> TYPE: RNA
<213> ORGANISM: Kaposi's sarcoma associated herpesvirus
```

```
<400> SEQUENCE: 54
ccggcaaguu ccaggcaucc ua                                          22

<210> SEQ ID NO 55
<211> LENGTH: 22
<212> TYPE: RNA
<213> ORGANISM: Kaposi's sarcoma associated herpesvirus

<400> SEQUENCE: 55
ccuagaguac ugcgguuuag cu                                          22

<210> SEQ ID NO 56
<211> LENGTH: 22
<212> TYPE: RNA
<213> ORGANISM: Kaposi's sarcoma associated herpesvirus

<400> SEQUENCE: 56
ucagcuaggc cucaguauuc ua                                          22

<210> SEQ ID NO 57
<211> LENGTH: 22
<212> TYPE: RNA
<213> ORGANISM: Kaposi's sarcoma associated herpesvirus

<400> SEQUENCE: 57
cgcugccguc cucagaaugu ga                                          22

<210> SEQ ID NO 58
<211> LENGTH: 22
<212> TYPE: RNA
<213> ORGANISM: Kaposi's sarcoma associated herpesvirus

<400> SEQUENCE: 58
gugucacauu cugugaccgc ga                                          22

<210> SEQ ID NO 59
<211> LENGTH: 22
<212> TYPE: RNA
<213> ORGANISM: Kaposi's sarcoma associated herpesvirus

<400> SEQUENCE: 59
cuuacaccca guuccugua au                                           22

<210> SEQ ID NO 60
<211> LENGTH: 22
<212> TYPE: RNA
<213> ORGANISM: Kaposi's sarcoma associated herpesvirus

<400> SEQUENCE: 60
gagcgccagc aacaugggau ca                                          22

<210> SEQ ID NO 61
<211> LENGTH: 22
<212> TYPE: RNA
<213> ORGANISM: Kaposi's sarcoma associated herpesvirus

<400> SEQUENCE: 61
ucggacacag gcuaagcauu aa                                          22

<210> SEQ ID NO 62
<211> LENGTH: 22
<212> TYPE: RNA
<213> ORGANISM: Kaposi's sarcoma associated herpesvirus
```

-continued

```
<400> SEQUENCE: 62
cgugcucucu cagucgcgcc ua                                              22

<210> SEQ ID NO 63
<211> LENGTH: 21
<212> TYPE: RNA
<213> ORGANISM: Kaposi's sarcoma-associated herpesvirus

<400> SEQUENCE: 63
ucgcggucac agaaugugac a                                               21

<210> SEQ ID NO 64
<211> LENGTH: 23
<212> TYPE: RNA
<213> ORGANISM: Kaposi's sarcoma-associated herpesvirus

<400> SEQUENCE: 64
ucacauucug aggacggcag cga                                             23

<210> SEQ ID NO 65
<211> LENGTH: 23
<212> TYPE: RNA
<213> ORGANISM: Kaposi's sarcoma-associated herpesvirus

<400> SEQUENCE: 65
auuacaggaa acugggugua agc                                             23

<210> SEQ ID NO 66
<211> LENGTH: 21
<212> TYPE: RNA
<213> ORGANISM: Kaposi's sarcoma-associated herpesvirus

<400> SEQUENCE: 66
ugaucccaug uugcuggcgc u                                               21

<210> SEQ ID NO 67
<211> LENGTH: 23
<212> TYPE: RNA
<213> ORGANISM: Kaposi's sarcoma-associated herpesvirus

<400> SEQUENCE: 67
uaggaugccu ggaacuugcc ggu                                             23

<210> SEQ ID NO 68
<211> LENGTH: 22
<212> TYPE: RNA
<213> ORGANISM: Human Cytomegalovirus

<400> SEQUENCE: 68
uaacuagccu ucccgugaga gu                                              22

<210> SEQ ID NO 69
<211> LENGTH: 22
<212> TYPE: RNA
<213> ORGANISM: Human Cytomegalovirus

<400> SEQUENCE: 69
ucaccagaau gcuaguuugu ag                                              22

<210> SEQ ID NO 70
<211> LENGTH: 22
<212> TYPE: RNA
<213> ORGANISM: Human Cytomegalovirus
```

<400> SEQUENCE: 70
ucguugaaga caccuggaaa ga                                               22

<210> SEQ ID NO 71
<211> LENGTH: 22
<212> TYPE: RNA
<213> ORGANISM: Human Cytomegalovirus

<400> SEQUENCE: 71
aagugacggu gagauccagg cu                                               22

<210> SEQ ID NO 72
<211> LENGTH: 22
<212> TYPE: RNA
<213> ORGANISM: Human Cytomegalovirus

<400> SEQUENCE: 72
ucguccuccc cuucuucacc gc                                               22

<210> SEQ ID NO 73
<211> LENGTH: 22
<212> TYPE: RNA
<213> ORGANISM: Human Cytomegalovirus

<400> SEQUENCE: 73
ugacaagccu gacgagagcg uu                                               22

<210> SEQ ID NO 74
<211> LENGTH: 22
<212> TYPE: RNA
<213> ORGANISM: Human Cytomegalovirus

<400> SEQUENCE: 74
uuaugauagg ugugacgaug uc                                               22

<210> SEQ ID NO 75
<211> LENGTH: 22
<212> TYPE: RNA
<213> ORGANISM: Human Cytomegalovirus

<400> SEQUENCE: 75
aaccgcucag uggcucggac cg                                               22

<210> SEQ ID NO 76
<211> LENGTH: 22
<212> TYPE: RNA
<213> ORGANISM: Human Cytomegalovirus

<400> SEQUENCE: 76
agcggucugu ucagguggau ga                                               22

<210> SEQ ID NO 77
<211> LENGTH: 22
<212> TYPE: RNA
<213> ORGANISM: Human Cytomegalovirus

<400> SEQUENCE: 77
auccacuugg agagcucccg cg                                               22

<210> SEQ ID NO 78
<211> LENGTH: 22
<212> TYPE: RNA
<213> ORGANISM: Human Cytomegalovirus

```
<400> SEQUENCE: 78
gauugugccc ggaccguggg cg                                          22

<210> SEQ ID NO 79
<211> LENGTH: 68
<212> TYPE: RNA
<213> ORGANISM: Human Cytomegalovirus

<400> SEQUENCE: 79
ccugucuaac uagccuuccc gugagaguuu augaacaugu aucucaccag aaugcuaguu   60
uguagagg                                                          68

<210> SEQ ID NO 80
<211> LENGTH: 68
<212> TYPE: RNA
<213> ORGANISM: Human Cytomegalovirus

<400> SEQUENCE: 80
ccugucuaac uagccuuccc gugagaguuu augaacaugu aucucaccag aaugcuaguu   60
uguagagg                                                          68

<210> SEQ ID NO 81
<211> LENGTH: 75
<212> TYPE: RNA
<213> ORGANISM: Human Cytomegalovirus

<400> SEQUENCE: 81
ccacgucguu gaagacaccu ggaaagagga cguucgcucg ggcacguucu uuccaggugu   60
uuucaacgug cgugg                                                  75

<210> SEQ ID NO 82
<211> LENGTH: 67
<212> TYPE: RNA
<213> ORGANISM: Human Cytomegalovirus

<400> SEQUENCE: 82
gacagccucc ggaucacaug guuacucagc gucugccagc cuaagugacg gugagaucca   60
ggcuguc                                                           67

<210> SEQ ID NO 83
<211> LENGTH: 72
<212> TYPE: RNA
<213> ORGANISM: Human Cytomegalovirus

<400> SEQUENCE: 83
agcaggugag guuggggcgg acaacguguu gcggauugug gcgagaacgu cguccucccc   60
uucuucaccg cc                                                     72

<210> SEQ ID NO 84
<211> LENGTH: 66
<212> TYPE: RNA
<213> ORGANISM: Human Cytomegalovirus

<400> SEQUENCE: 84
ugaacgcuuu cgucuguguu uucaugcagc uuuuacagac caugacaagc cugacgagag   60
cguuca                                                            66

<210> SEQ ID NO 85
<211> LENGTH: 65
<212> TYPE: RNA
```

<213> ORGANISM: Human Cytomegalovirus

<400> SEQUENCE: 85
ggaggcuuuc gccacaccua uccugaaagc guugcauucu uuaugauagg ugugacgaug    60
ucuuu    65

<210> SEQ ID NO 86
<211> LENGTH: 70
<212> TYPE: RNA
<213> ORGANISM: Human Cytomegalovirus

<400> SEQUENCE: 86
ugugaaccgc ucaguggcuc ggaccgccgg cuguuucugc gcaccggucc gaacgcuagg    60
ucgguucuca    70

<210> SEQ ID NO 87
<211> LENGTH: 90
<212> TYPE: RNA
<213> ORGANISM: Human Cytomegalovirus

<400> SEQUENCE: 87
cgguuagcgg ucguucagg uggaugaggg cucuucacgg ucgggcacuc ggcugugccu    60
gucauccacu uggagagcuc ccgcgguccg    90

<210> SEQ ID NO 88
<211> LENGTH: 90
<212> TYPE: RNA
<213> ORGANISM: Human Cytomegalovirus

<400> SEQUENCE: 88
cgguuagcgg ucguucagg uggaugaggg cucuucacgg ucgggcacuc ggcugugccu    60
gucauccacu uggagagcuc ccgcgguccg    90

<210> SEQ ID NO 89
<211> LENGTH: 70
<212> TYPE: RNA
<213> ORGANISM: Human Cytomegalovirus

<400> SEQUENCE: 89
cacgguugau ugugcccgga ccgugggcgc gacgaaaccc accgucacgg uccgagcaca    60
uccaaacgug    70

<210> SEQ ID NO 90
<211> LENGTH: 22
<212> TYPE: RNA
<213> ORGANISM: Human Cytomegalovirus

<400> SEQUENCE: 90
acucucacgg gaaggcuagu ua    22

<210> SEQ ID NO 91
<211> LENGTH: 22
<212> TYPE: RNA
<213> ORGANISM: Human Cytomegalovirus

<400> SEQUENCE: 91
cuacaaacua gcauucuggu ga    22

<210> SEQ ID NO 92
<211> LENGTH: 22
<212> TYPE: RNA

<213> ORGANISM: Human Cytomegalovirus

<400> SEQUENCE: 92
ucuuuccagg ugucuucaac ga                                              22

<210> SEQ ID NO 93
<211> LENGTH: 22
<212> TYPE: RNA
<213> ORGANISM: Human Cytomegalovirus

<400> SEQUENCE: 93
agccuggauc ucaccgucac uu                                              22

<210> SEQ ID NO 94
<211> LENGTH: 22
<212> TYPE: RNA
<213> ORGANISM: Human Cytomegalovirus

<400> SEQUENCE: 94
gcggugaaga agggaggac ga                                               22

<210> SEQ ID NO 95
<211> LENGTH: 22
<212> TYPE: RNA
<213> ORGANISM: Human Cytomegalovirus

<400> SEQUENCE: 95
aacgcucucg ucaggcuugu ca                                              22

<210> SEQ ID NO 96
<211> LENGTH: 22
<212> TYPE: RNA
<213> ORGANISM: Human Cytomegalovirus

<400> SEQUENCE: 96
gacaucguca caccuaucau aa                                              22

<210> SEQ ID NO 97
<211> LENGTH: 22
<212> TYPE: RNA
<213> ORGANISM: Human Cytomegalovirus

<400> SEQUENCE: 97
cgguccgagc cacugagcgg uu                                              22

<210> SEQ ID NO 98
<211> LENGTH: 22
<212> TYPE: RNA
<213> ORGANISM: Human Cytomegalovirus

<400> SEQUENCE: 98
ucauccaccu gaacagaccg cu                                              22

<210> SEQ ID NO 99
<211> LENGTH: 22
<212> TYPE: RNA
<213> ORGANISM: Human Cytomegalovirus

<400> SEQUENCE: 99
cgcgggagcu cuccaagugg au                                              22

<210> SEQ ID NO 100
<211> LENGTH: 22
<212> TYPE: RNA

```
<213> ORGANISM: Human Cytomegalovirus

<400> SEQUENCE: 100
cgcccacggu ccgggcacaa uc                                    22

<210> SEQ ID NO 101
<211> LENGTH: 20
<212> TYPE: RNA
<213> ORGANISM: Human Cytomeglovirus

<400> SEQUENCE: 101
uaacuagccu ucccgugaga                                       20

<210> SEQ ID NO 102
<211> LENGTH: 21
<212> TYPE: RNA
<213> ORGANISM: Human Cytomeglovirus

<400> SEQUENCE: 102
ucguccuccc cuucuucacc g                                     21

<210> SEQ ID NO 103
<211> LENGTH: 21
<212> TYPE: RNA
<213> ORGANISM: Human Cytomeglovirus

<400> SEQUENCE: 103
ugacaagccu gacgagagcg u                                     21

<210> SEQ ID NO 104
<211> LENGTH: 21
<212> TYPE: RNA
<213> ORGANISM: Human Cytomeglovirus

<400> SEQUENCE: 104
aaccgcucag uggcucggac c                                     21

<210> SEQ ID NO 105
<211> LENGTH: 23
<212> TYPE: RNA
<213> ORGANISM: Human Cytomeglovirus

<400> SEQUENCE: 105
auccacuugg agagcucccg cgg                                   23
```

US 8,088,902 B2

DNA VIRUS MICRORNA AND METHODS FOR INHIBITING SAME

This application is a continuation-in-part of U.S. patent application Ser. No. 10/925,363 filed on Aug. 24, 2004 now abandoned, which is a continuation-in-part of U.S. patent application Ser. No. 10/819,098 filed on Apr. 5, 2004 now U.S. Pat. No. 7,416,842. The specifications of U.S. patent application Ser. Nos. 10/925,363 and 10/819,098 are hereby incorporated by reference in their entirety.

This invention described in this application was made with funds from the National Institutes of Health, Grant Number R01-GM068476-01. The United States Government has certain rights in this invention.

BACKGROUND OF THE INVENTION

MicroRNAs are small RNA molecules of about 22 nucleotides. These microRNA molecules can control gene expression in a sequence specific manner in a wide variety of organisms.

In many organisms, RNA silencing mediated by double-stranded RNA (dsRNA), such as siRNA and microRNA, is part of an innate immune response against RNA viruses and transposable elements. Counter defense strategies to thwart the host response were found in, for example, plant viruses and the insect Flock House virus. These viruses express inhibitors, e.g., dsRNA-binding proteins, that interfere with the host cell RNA silencing machinery.

For example, microRNAs are reported to block translation after partially hybridizing to the non-coding 3' region of mRNAs of target genes. The genes targeted by microRNAs largely remain to be characterized. However, there is growing evidence that microRNAs are implicated in various diseases and illnesses. For instance, drosophila microRNAs have been shown to target genes involved in apoptosis, and B-cell chronic lymphocytic leukemia has been linked to the deletion of two microRNAs.

However, to date, the existence of microRNA encoded by mammalian viruses have not been reported. Identifying mammalian virus microRNAs, and, if they exist, understanding their biological function would facilitate the development of new anti-viral drugs.

Therefore, there is a need to identify viral microRNAs, and for new materials and methods that can help elucidate the function of known and future virus microRNAs.

Due to the ability of microRNAs to induce RNA degradation or repress translation of mRNA which encode important proteins, there is also a need for novel molecules that inhibit DNA virus microRNA-induced cleavage or translation repression of target mRNAs.

SUMMARY OF THE INVENTION

In one embodiment, the invention relates to an isolated nucleic acid molecule comprising the sequence of a DNA virus microRNA.

In another embodiment, the invention relates to an isolated single stranded DNA virus microRNA molecule. The molecule comprises a minimum of ten moieties and a maximum of fifty moieties on a molecular backbone, the molecular backbone comprising backbone units. Each moiety comprises a base bonded to a backbone unit wherein at least ten contiguous bases have the same sequence as a sequence of bases in a DNA virus microRNA molecule, except that up to thirty percent of the bases pairs may be wobble base pairs, and up to 10% of the contiguous bases are additions, deletions, mismatches, or combinations thereof, and no more than fifty percent of the contiguous moieties contain deoxyribonuleotide backbone units.

In a further embodiment, the invention relates to an isolated single stranded anti-DNA virus microRNA molecule. The anti-DNA virus microRNA molecule comprises a minimum of ten moieties and a maximum of fifty moieties on a molecular backbone, the molecular backbone comprising backbone units. Each moiety comprising a base bonded to a backbone unit, each base forming a Watson-Crick base pair with a complementary base wherein at least ten contiguous bases have a sequence complementary to a contiguous sequence of bases in a DNA virus microRNA molecule, except that up to thirty percent of the bases pairs may be wobble base pairs, and up to 10% of the contiguous bases are additions, deletions, mismatches, or combinations thereof; no more than fifty percent of the contiguous moieties contain deoxyribonuleotide backbone units; and the molecule is capable of inhibiting microRNP activity.

In yet a further embodiment, the invention relates to a method for inhibiting microRNP activity in a cell. The microRNP comprises a DNA virus microRNA molecule, the DNA virus microRNA molecule comprising a sequences of bases complementary to the sequence of bases in a single stranded anti-DNA virus microRNA molecule. The method comprises introducing into the cell a single-stranded anti-DNA virus microRNA molecule comprising a sequence of a minimum of ten moieties and a maximum of fifty moieties on a molecular backbone, the molecular backbone comprising backbone units, each moiety comprising a base bonded to a backbone unit, each base forming a Watson-Crick base pair with a complementary base, wherein at least ten contiguous bases of the anti-DNA virus microRNA molecule are complementary to the DNA virus microRNA, except that up to thirty percent of the bases may be substituted by wobble base pairs, and up to ten percent of the at least ten moieties are addition, deletions, mismatches, or combinations thereof, and no more than fifty percent of the contiguous moieties contain deoxyribonuleotide backbone units.

In yet another embodiment, the invention relates to a method for treating a DNA virus infection in a mammal in need thereof. The method comprises introducing into the mammal an anti-DNA virus microRNA molecule.

In another embodiment, the invention relates to an isolated microRNP comprising an isolated nucleic acid molecule described herein.

In a further embodiment, the invention relates to an isolated microRNP comprising an isolated single stranded DNA virus microRNA molecule.

In yet a further embodiment, the invention relates to an isolated nucleic acid sequence comprising any one of the sequence of a DNA virus microRNA shown in Tables A1 or A2.

In yet another embodiment, the invention relates to an isolated single stranded DNA virus microRNA molecule comprising a minimum of ten moieties and a maximum of fifty moieties on a molecular backbone. The molecular backbone comprising backbone units, each moiety comprising a base bonded to a backbone unit wherein: at least ten contiguous bases have the same sequence as any one of the sequence of bases in a DNA virus microRNA molecule shown in Tables A1 or A2, except that up to thirty percent of the bases pairs may be wobble base pairs, and up to 10% of the contiguous bases are additions, deletions, mismatches, or combinations thereof; and no more than fifty percent of the contiguous moieties contain deoxyribonuleotide backbone units.

In another embodiment, the invention relates to an isolated single stranded anti-DNA virus microRNA molecule comprising a minimum of ten moieties and a maximum of fifty moieties on a molecular backbone. The molecular backbone comprising backbone units, each moiety comprising a base bonded to a backbone unit, each base forming a Watson-Crick base pair with a complementary base wherein at least ten contiguous bases have a sequence complementary to a contiguous sequence of bases in the sequence of bases in any one of the DNA virus microRNA molecule shown in Tables A1 or A2, except that up to thirty percent of the bases pairs may be wobble base pairs, and up to 10% of the contiguous bases are additions, deletions, mismatches, or combinations thereof; no more than fifty percent of the contiguous moieties contain deoxyribonuleotide backbone units; and the molecule is capable of inhibiting microRNP activity.

DESCRIPTION OF THE FIGURES

FIG. 1 shows the modified nucleotide units discussed in the specification. B denotes any one of the following nucleic acid bases: adenosine, cytidine, guanosine, thymine, or uridine.

FIG. 2. EBV expresses microRNAs. (A) Diagram of the microRNA containing segments of the EBV genome. Latent genes are indicated with white boxes, lytic genes with black boxes, previously known non-coding RNAs with blue and newly identified microRNAs with red. Promoters active at latent stages (I, II, or III) are illustrated as white pennants, those active at lytic stage as black pennants, and those active at all stages as gray pennants. The intronic segments within the BARTs region are indicated as dashed lines, the exonic segments with bold bars. (B) Predicted fold-back precursors of the EBV microRNAs. The mature microRNA is highlighted in red. An asterisk is used to denote a low abundant small RNA that was cloned from the strand opposite to the microRNA-BHRF1-2 strand. (C) Northern blots for EBV microRNAs using total RNA isolated from uninfected BL-41 (−) and EBV-infected BL41/95 (+) cells. The expression of human miR-16 (Table S1) was also examined for reference. The position of migration of the mature microRNAs (miR) and its fold-back precursors (miR-L) are indicated. Equal loading of the gel before transfer to the membrane was monitored by ethidium bromide staining of the tRNA band. (D) Northern blots for EBV microRNAs using total RNA isolated from various Hodgkin and Burkitt lymphoma cell lines. The latency stage for EBV positive lines is indicated in parentheses. The numbers below the miR signals indicate relative signal intensity with respect to BL41/95 signals after normalizing for gel loading using the U6 snRNA signal.

FIG. 6. Genomic positions and secondary structures of HCMV mRNAs. (A) Diagram of the mRNA-containing fragments of the HCMV genome. Terminal repeats are shown as grey boxes and triangles. Cloned mRNAs are shown as dotted red lines. The mRNAs encoded from the (+)-strand of the genome are shown above the genome, those deriving from the (−)-strand of the genome are shown below. The arrows indicate the orientation of the viral ORF's. (B) Predicated foldback precursors of HCMV microRNAs. The cloned mature microRNAs are highlighted in red. An asterisk is used to highlight low-abundance small RNA that was cloned from the strand opposite from miR-UL1 strand.

DETAILED DESCRIPTION OF THE INVENTION

Figure 3:
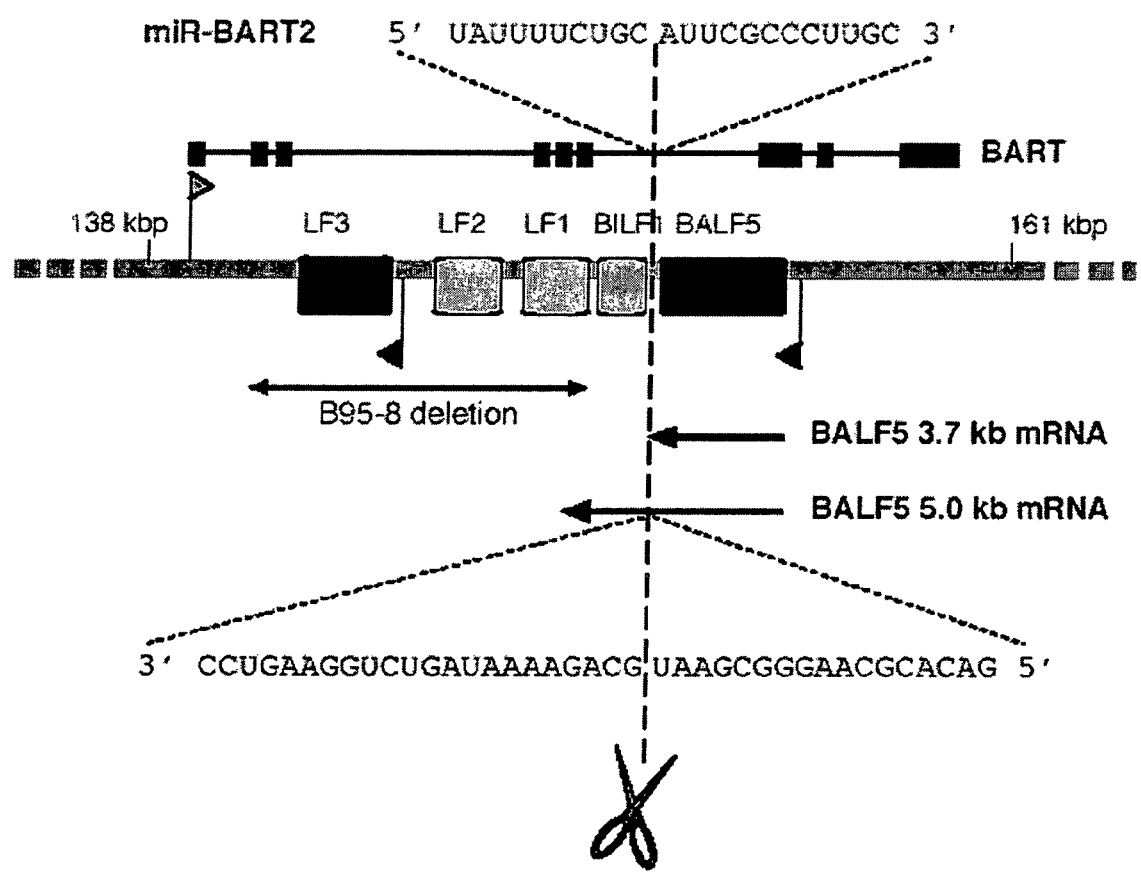
FIG. 3. Schematic representation of miR-BART2-guided cleavage of BALF5 mRNA. Lytic genes are shown as black boxes and genes for which the expression has not been characterized are indicated in gray (GenBank entry V01555). The miR-BART2 sequence is aligned relative to the nucleotide sequence and the processing site of the BALF5 mRNA. The prediction position of BALF5 mRNA cleavage coincides with the mapped terminus of the 3.7 kb processed form.

The inventors have discovered DNA virus-encoded microRNAs. Thus, in one embodiment, the invention relates to an isolated single stranded DNA virus microRNA molecule.

MicroRNA molecules are known in the art (see, for example, Bartel, *Cell,* 2004, 116, 281-297 for a review on microRNA molecules). The article by Bartel is hereby incorporated by reference. Such molecules are derived from genomic loci and are produced from specific microRNA genes.

Mature microRNA molecules are processed from precursor transcripts that form local hairpin structures. The hairpin structures are typically cleaved by an enzyme known as Dicer, generating thereby one microRNA duplex. See the above reference by Bartel.

Usually, one of the two strands of a microRNA duplex is packaged in a microRNA ribonucleoprotein complex (microRNP). A microRNP in, for example, humans, also includes the proteins eIF2C2, helicase, e.g., Gemin3, and Gemin 4.

Unmodified DNA Virus microRNA Molecules

In one embodiment, the invention relates to an isolated nucleic acid molecule comprising a DNA virus microRNA sequence or a DNA virus hairpin precursor sequence. In addition to the sequence of the DNA virus microRNA or hairpin precursor, the nucleic acid molecule may also have one or more additional nucleotides. Any nucleotide can be added. There is no upper limit to the additional number of nucleotides. Typically, no more than about 500 nucleotides, and preferably no more than about 300 nucleotides are added to the DNA virus microRNA sequence or hairpin precursor sequence. In one embodiment, the DNA virus microRNA is part of a hairpin precursor sequence of fragment thereof.

The DNA virus microRNA can be inserted into a vector, such as, for example, a recombinant vector. Typically, to construct such a recombinant vector containing a DNA virus microRNA, the hairpin precursor sequence which contains the DNA virus microRNA sequence, is incorporated into the vector. See for example, Chen et al. *Science* 2004, 303:83-86.

The recombinant vector may be any recombinant vector, such as a plasmid, a cosmid or a phage. Recombinant vectors generally have an origin of replication. The vector may be, for example, a viral vector, such as an adenovirus vector or an adeno-associated virus (AAV) vector. See for example: Ledley 1996, *Pharmaceutical Research* 13:1595-1614 and Verma et al. *Nature* 1997, 387:239-242.

The vector may further include a selectable marker, such as for instance a drug resistance marker or a detectable gene marker, such as β-galactosidase.

In a preferred embodiment, the nucleic acid molecule consists of a DNA virus microRNA sequence or a hairpin precursor sequence. In another preferred embodiment, the nucleic acid molecule consists of any one of the DNA virus microRNA sequence or hairpin precursor sequence shown in Table A, Table A1 or Table A2.

The DNA virus can be any DNA virus known to those skilled in the art. Preferably, the DNA virus infects mammalian cells. Examples of mammals include laboratory animals, such as dogs and cats, farm animals, such as cows, horses and sheeps, laboratory animals, such as rats, mice and rabbits, and primates, such as monkeys and humans.

The DNA virus can be a single stranded or double stranded DNA virus. Examples of single stranded and double stranded DNA viruses are listed in Table B.

In one embodiment, the DNA virus is Epstein barr virus (EBV). Examples of EBV microRNA's and the corresponding hairpin precursor sequences are shown in Table A.

In another embodiment, the DNA virus is Kaposi's sarcoma-associated herpesvirus, also known as herpesvirus 8 (KSHV). Examples of KSHV microRNA's and the corresponding hairpin precursor sequences are shown in Table A1.

In yet another embodiment, the DNA virus is cytomegalovirus (HCMV). Examples of HCMV microRNA's and the corresponding hairpin precursor sequences are shown in Table A2.

The sequence of the isolated DNA virus microRNA molecules can be a DNA or RNA molecule. Sequences of nucleic acid molecules shown in Tables A, A1 and A2 are shown having uracil bases. Uracil bases occur in unmodified RNA molecules. The invention also includes unmodified DNA molecules. The sequence of bases of the unmodified DNA molecule is the same as the unmodified RNA molecules, except that in the unmodified DNA molecule, the uracil bases are replaced with thymine bases.

TABLE A

EBV microRNA's and Hairpin Precursor Sequences

| Virus | microRNA Sequence 5' → 3' | Hairpin Precursor microRNA Sequence* (5' → 3') |
|---|---|---|
| EBV | UAACCUGAUCAGCCCCGGAGUU (SEQ. ID. NO. 1) | UAUUAACCUGAUCAGCCCCGGAGUUGCCUGUUUUCAU CACUAACCCCGGGCCUGAAGAGGUUGACAA (SEQ. ID. NO. 6) |
| | UAUCUUUUGCGGCAGAAAUUGAA (SEQ. ID. NO. 2) | C*UUUUAAAUUCUGUUGCAGCAGAUAGCUGAUACCCAAU* GUUAUCUUUUGCGGCAGAAAUUGAAAG (SEQ. ID. NO. 7) |
| | UAACGGGAAGUGUGUAAGCACAC (SEQ. ID. NO. 3) | UCUAACGGGAAGUGUGUAAGCACACACGUAAUUUGC AAGCGGUGCUUCACGCUCUUCGUUAAAAU (SEQ. ID. NO. 8) |
| | UCUUAGUGGAAGUGACGUGCU (SEQ. ID. NO. 4) | CGGGGUCUUAGUGGAAGUGACGUGCUGUGAAUACAG GUCCAUAGCACCGCUAUCCACUAUGUCUCGCCCG (SEQ. ID. NO. 9) |
| | UAUUUUCUGCAUUCGCCCUUGC (SEQ. ID. NO. 5) | ACUAUUUUCUGCAUUCGCCCUUGCGUGUCCAUUGUU GCAAGGAGCGAUUUGGAGAAAAUAAA (SEQ. ID. NO. 10) |

*In bold, mature microRNA sequence. In italics, a low abundant sequence corresponding to the non-functional strand of the microRNA

TABLE A1

KSHV microRNA's and Hairpin Precursor Sequences

| Virus | microRNA Sequence 5' → 3' | Hairpin Precursor microRNA Sequence* (5' → 3') |
|---|---|---|
| KSHV | UAGUGUUGUCCCCCCGAGUGGC (SEQ. ID. NO. 18) | CUGGAGGCUUGGGGCGAUACCACCACUCGUUUGUCUGUUG GCGAUUAGUGUUGUCCCCCCGAGUGGCCAG (SEQ. ID. NO. 33) |
| | UGGUGUUGUCCCCCCGAGUGGC (SEQ. ID. NO. 18) | CUGGAGGCUUGGGGCGAUACCACCACUCGUUUGUCUGUUG GCGAUUGGUGUUGUCCCCCCGAGUGGCCAG (SEQ. ID. NO. 34) |
| | ACCCAGCUGCGUAAACCCCGCU (SEQ. ID. NO. 20) | GGGUCUACCCAGCUGCGUAAACCCCGCUGCGUAAACACA GCUGGGUAUACGCAGCUGCGUAAACCC (SEQ. ID. NO. 35) |
| | CUGGGUAUACGCAGCUGCGUAA (SEQ. ID. NO. 21) | GGUCUACCCAGCUGCGUAAACCCCGCUGCGUAAACAGC UGGGUAUACGCAGCUGCGUAAACCC (SEQ. ID. NO. 36) |

TABLE A1-continued

KSHV microRNA's and Hairpin Precursor Sequences

| Virus | microRNA Sequence 5' → 3' | Hairpin Precursor microRNA Sequence* (5' → 3') |
|---|---|---|
| | CCAGCAGCACCUAAUCCAUCGG (SEQ. ID. NO. 22) | CUUGUCCAGCAGCACCUAAUCCAUCGGCGGUCGGGCUGA UGGUUUUCGGGCUGUUGAGCGAG (SEQ. ID. NO. 37) |
| | UGAUGGUUUUCGGGCUGUUGAG (SEQ. ID. NO. 23) | CUUGUCCAGCAGCACCUAAUCCAUCGGCGGUCGGGUGAU GGUUUUCGGGCUGUUGAGCGAG (SEQ. ID. NO. 38) |
| | UAGGAUGGCUGGAACUUGCCGG (SEQ. ID. NO. 24) | UGACCUAGGUAGUCCCUGGUGCCCUAAGGGUCUACAUCAA GCACUUAGGAUGCCUGGAACUUGCCGGUCA (SEQ. ID. NO. 39) |
| | AGCUAAACCGCAGUACUCUAGG (SEQ. ID. NO. 25) | AUAACUAGCUAAACCGCAGUACUCUAGGGCAUUCAUUUG UUACAUAGAAUACUGAGGCCUAGCUGAUUAU (SEQ. ID. NO. 40) |
| | UAGAAUACUGAGGCCUAGCUGA (SEQ. ID. NO. 26) | AUAACUAGCUAAACCGCAGUACUCUAGGGCAUUCAUUUGU UACAUAGAAUACUGAGGCCUAGCUGAUUAU (SEQ. ID. NO. 41) |
| | UCACAUUCUGAGGACGGCAGCG (SEQ. ID. NO. 27) | GGCUAUCACAUUCUGAGGACGGCAGCGACGUGUGUCUAA CGUCAACGUCGCGGUCACAGAAUGUGACACC (SEQ. ID. NO. 42) |
| | UCGCGGUCACAGAAUGUGACAC (SEQ. ID. NO. 28) | GGCUAUCACAUUCUGAGGACGGCAGCGACGUGUGUCUAAG GUCAACGUCGCGGUCACAGAAUGUGACACC (SEQ. ID. NO. 43) |
| | AUUACAGGAAACUGGGUGUAAG (SEQ. ID. NO. 29) | GGAUUACAGGAAACUGGGUGUAAGCUGUACAUAAUCCCC GGCAGCACCUGUUUCCUGCAACCCUCGU (SEQ. ID. NO. 44) |
| | UGAUCCCAUGUUGCUGGCGCUC (SEQ. ID. NO. 30) | GCGUUGAGCGCCACCGGACGGGGAUUUAUGCUGUAUCUUA CUACCAUGAUCCCAUGUUGCUGGCGCUCACGG (SEQ. ID. NO. 45) |
| | UUAAUGCUUAGCCUGUGUCCGA (SEQ. ID. NO. 31) | CGCUUUGGUCACAGCUUAAACAUUUCUAGGGCGGUGUUAU GAUCCUUAAUGCUUAGCCUGUGUCCGAUGCG (SEQ. ID. NO. 46) |
| | UAGGCGCGACUGAGAGAGCACG (SEQ. ID. NO. 32) | CGCGCACUCCCUCACUAACGCCCCGCUUUUGUCUGUUGGA AGCAGCUAGGCGCGACUGAGAGAGCACGCG (SEQ. ID. NO. 47) |

*In bold, the mature microRNA sequence.

TABLE A2

HCMV microRNA's and Hairpin Precursor Sequences

| Virus | microRNA Sequence 5' → 3' | Hairpin Precursor microRNA Sequence* (5' → 3') |
|---|---|---|
| HCMV | UAACUAGCCUUCCCGUGAGAGU (SEQ. ID. NO. 68) | CCUGUCUAACUAGCCUUCCCGUGAGAGUUUAUGAACAUG UAUCUCACCAGAAUGCUAGUUUGUAGAGG (SEQ. ID. NO. 79) |
| | UCACCAGAAUGCUAGUUUGUAG (SEQ. ID. NO. 69) | CCUGUCUAACUAGCCUUCCCGUGAGAGUUUAUGAACAUGU AUCUCACCAGAAUGCUAGUUUGUAGAGG (SEQ. ID. NO. 80) |
| | UCGUUGAAGACACCUGGAAAGA (SEQ. ID. NO. 70) | CCACGUCGUUGAAGACACCUGGAAAGAGGACGUUCGGUC GGGCACGUUCUUUCCAGGUGUUUUCAACGUGCGUGG (SEQ. ID. NO. 81) |
| | AAGUGACGGUGAGAUCCAGGCU (SEQ. ID. NO. 71) | GACAGCCUCCGGAUCACAUGGUUACUCAGCGUCUGCCAGC CUAAGUGACGGUGAGAUCCAGGCUGUC (SEQ. ID. NO. 82) |
| | UCGUCCUCCCCUUCUUCACCGC (SEQ. ID. NO. 72) | AGCAGGUGAGGUUGGGCGACAACGUGUUGCGGAUUGU GGCGAGAACGUCUCCUCCCCUUCUUCACCGCC (SEQ. ID. NO. 83) |

TABLE A2-continued

HCMV microRNA's and Hairpin Precursor Sequences

| Virus | microRNA Sequence 5' → 3' | Hairpin Precursor microRNA Sequence* (5' → 3') |
|---|---|---|
| | UGACAAGCCUGACGAGAGCGUU (SEQ. ID. NO. 73) | UGAACGCUUUCGUCGUGUUUUUCAUGCAGCUUUUACAGAC CAUGACAAGCCUGACGAGAGCGUUCA (SEQ. ID. NO. 84) |
| | UUAUGAUAGGUGUGACGAUGUC (SEQ. ID. NO. 74) | GGAGGCUUUCGCCACACCUAUCCUGAAAGCGUUGCAUUCU UUAUGAUAGGUGUGACGAUGUCUUU (SEQ. ID. NO. 85) |
| | AACCGCUCAGUGGCUCGGACCG (SEQ. ID. NO. 75) | UGUGAACCGCUCAGUGGCUCGGACCGCCGGCUGUUUCUG CGCACCGGUCCGAACGCUAGGUCGGUUCUCA (SEQ. ID. NO. 86) |
| | AGCGGUCUGUUCAGGUGGAUGA (SEQ. ID. NO. 76) | CGGUUAGCGGUCUGUUCAGGUGGAUGAGGGCUCUUCAGG GUCGGGCACUCGGCUGUGCCUGUCAUCCACUUGGAGAGCU CCCGCGGUCCG (SEQ. ID. NO. 87) |
| | AUCCACUUGGAGAGCUCCCGCG (SEQ. ID. NO. 77) | CGGUUAGCGGUCUGUUCAGGUGGAUGAGGGCUCUUCACGG UCGGGCACUCGGCUGUGCCUGUCAUCCACUUGGAGAGCU CCCGCGGUCCG (SEQ. ID. NO. 88) |
| | GAUUGUGCCCGGACCGUGGGCG (SEQ. ID. NO. 78) | CACGGUUGAUUGUGCCCGGACCGUGGGCGCGACGAAACC CACCGUCACGGUCCGAGCACAUCCAAACGUG (SEQ. ID. NO. 89) |

*In bold, the mature microRNA sequence

TABLE B

Single Stranded and Double Stranded DNA Viruses

| Family | Subfamily | Genus | Type species |
|---|---|---|---|
| *The dsDNA Viruses* | | | |
| Poxviridae | Chordopoxvirinae | Orthopoxvirus | Vaccinia virus |
| | | Parapoxvirus | Orf virus |
| | | Leporipoxvirus | Myxoma virus |
| | | Molluscipoxvirus | Molluscum contagiosum virus |
| Herpesviridae | Alphaherpesvirinae | Simplexvirus | Human herpesvirus 1 |
| | | Varicellovirus | Human herpesvirus 3 |
| | Betaherpesvirinae | Cytomegalovirus | Human herpesvirus 5 (HCMV) |
| | | Muromegalovirus | Murid herpesvirus 1 |
| | | Roseolovirus | Human herpesvirus 6 |
| | Gammaherpesvirinae | Lymphocryptovirus | Human herpesvirus 4 (EBV) |
| | | Rhadinovirus | Saimiriine herpesvirus 2 |
| | | Rhadinovirus | Human herpesvirus 8 (KSHV) |
| Adenoviridae | | Mastadenovirus | Human adenovirus C |
| Polyomaviridae | | Polyomavirus | Simian virus 40 |
| Papillomaviridae | | Papillomavirus | Cottontail rabbit papillomavirus |
| *The ssDNA Viruses* | | | |
| Parvoviridae | Parvovirinae | Parvovirus | Mice minute virus |
| | | Erythrovirus | B19 virus |
| | | Dependovirus | Adeno-associated virus 2 |

Analogs of DNA Virus microRNA Molecules

In another embodiment, the invention relates to analogs of DNA virus microRNAs or hairpin precursors described above, including those having the sequences shown in Table A, Table A1 or Table A2. In this embodiment, the DNA virus microRNA molecule comprises a minimum number of ten moieties, preferably a minimum of thirteen, more preferably a minimum of fifteen, even more preferably a minimum of eighteen, and most preferably a minimum of 21 moieties.

The DNA virus microRNA molecule comprises a maximum number of fifty moieties, preferably a maximum of forty, more preferably a maximum of thirty, even more preferably a maximum of twenty-five, and most preferably a maximum of twenty-three moieties. A suitable range of minimum and maximum numbers of moieties may be obtained by combining any of the above minima with any of the above maxima.

Each moiety comprises a base bonded to a backbone unit. In this specification, a base refers to any one of the nucleic acid bases present in DNA or RNA. The base can be a purine or pyrimidine. Examples of purine bases include adenine (A) and guanine (G). Examples of pyrimidine bases include thymine (T), cytosine (C) and uracil (U). Each base of the moiety forms a Watson-Crick base pair with a complementary base.

Watson-Crick base pairs as used herein refer to the hydrogen bonding interaction between, for example, the following bases: adenine and thymine (A-T); adenine and uracil (A-U); and cytosine and guanine (C-G). The adenine can be replaced with 2,6-diaminopurine without compromising base-pairing.

The backbone unit may be any molecular unit that is able to stably bind to a base and to form an oligomeric chain. Suitable backbone units are well known to those in the art.

For example, suitable backbone units include sugar-phosphate groups, such as the sugar-phosphate groups present in ribonucleotides, deoxyribonucleotides, phosphorothioate deoxyribose groups, N'3-N'5 phosphoroamidate deoxyribose groups, 2'O-alkyl-ribose phosphate groups, 2'-O-alkyl-alkoxy ribose phosphate groups, ribose phosphate group containing a methylene bridge, 2'-fluororibose phosphate groups, morpholino phosphoroamidate groups, cyclohexene groups, tricyclo phosphate groups, and amino acid molecules.

Preferably, the DNA virus microRNA molecule comprises at least one moiety which confers increased nuclease resistance. Such molecules comprise at least one moiety that is not recognized by a nuclease. Therefore, the nuclease resistance of the molecule is increased compared to a sequence containing only unmodified ribonucleotide, unmodified deoxyribonucleotide or both. Such modified moieties are well known in the art, and were reviewed, for example, by Kurreck, Eur. J. Biochem. 270, 1628-1644 (2003).

The nuclease resisted can be an exonuclease, an endonuclease, or both. The exonuclease can be a 3'→5' exonuclease or a 5'→3' exonuclease. Examples of 3'→5' human exonuclease include PNPT1, Werner syndrome helicase, RRP40, RRP41, RRP42, RRP45, and RRP46. Examples of 5'→3' exonuclease include XRN2, and FEN1. Examples of endonucleases include Dicer, Drosha, RNase4, Ribonuclease P, Ribonuclease H1, DHP1, ERCC-1 and OGG1. Examples of nucleases which function as both an exonuclease and an endonuclease include APE1 and EXO1.

A modified moiety can occur at any position in the DNA virus microRNA molecule. For example, to protect the DNA virus microRNA molecule against 3'→5' exonucleases, the molecule can have at least one modified moiety at the 3' end of the molecule and preferably at least two modified moieties at the 3' end. If it is desirable to protect the molecule against 5'→3' exonuclease, the DNA virus microRNA molecule can have at least one modified moiety and preferably at least two modified moieties at the 5' end of the molecule. The DNA virus microRNA molecule can also have at least one and preferably at least two modified moieties between the 5' and 3' end of the molecule to increase resistance of the molecule to endonucleases. Preferably, at least about 10%, more preferably at least about 25%, even more preferably at least about 50%, and further more preferably at least about 75%, and most preferably about 95% of the moieties are modified. In one embodiment, all of the moieties are nuclease resistant.

In another embodiment, the DNA virus microRNA molecule comprises at least one modified deoxyribonucleotide moiety. Suitable modified deoxyribonucleotide moieties are known in the art.

A suitable example of a modified deoxyribonucleotide moiety is a phosphorothioate deoxyribonucleotide moiety. See structure 1 in FIG. 1. A DNA virus microRNA molecule comprising phosphorothioate deoxyribonucleotide moieties is generally referred to as phosphorothioate (PS) DNA. See, for example, Eckstein, Antisense Nucleic Acids Drug Dev. 10, 117-121 (2000).

Another suitable example of a modified deoxyribonucleotide moiety is an N'3-N'5 phosphoroamidate deoxyribonucleotide moiety. See structure 2 in FIG. 1. An oligonucleotide molecule comprising phosphoroamidate deoxyribonucleotide moieties is generally referred to as phosphoroamidate (NP) DNA. See, for example, Gryaznov et al., J. Am. Chem. Soc. 116, 3143-3144 (1994).

In another embodiment, the molecule comprises at least one modified ribonucleotide moiety. Suitable modified ribonucleotide moieties are known in the art.

A suitable example of a modified ribonucleotide moiety is a ribonucleotide moiety that is substituted at the 2' position. The substituents at the 2' position may, for example, be a $C_1$ to $C_4$ alkyl group. The $C_1$ to $C_4$ alkyl group may be saturated or unsaturated, and unbranched or branched. Some examples of $C_1$ to $C_4$ alkyl groups include ethyl, isopropyl, and allyl. The preferred $C_1$ to $C_4$ alkyl group is methyl. See structure 3 in FIG. 1. An oligoribonucleotide molecule comprising ribonucleotide moieties substituted at the 2' position with a $C_1$ to $C_4$ alkyl group is generally referred to as a 2'-O—($C_1$-$C_4$ alkyl) RNA, e.g., 2'-O-methyl RNA (OMe RNA).

Another suitable example of a substituent at the 2' position of a modified ribonucleotide moiety is a $C_1$ to $C_4$ alkoxy-$C_1$ to $C_4$ alkyl group. The $C_1$ to $C_4$ alkoxy (alkyloxy) and $C_1$ to $C_4$ alkyl group may comprise any of the alkyl groups described above. The preferred $C_1$ to $C_4$ alkoxy-$C_1$ to $C_4$ alkyl group is methoxyethyl. See structure 4 in FIG. 1. An oligonucleotide molecule comprising more than one ribonucleotide moiety that is substituted at the 2' position with a C1 to $C_4$ alkoxy-$C_1$ to $C_4$ alkyl group is referred to as a 2'-O—($C_1$ to $C_4$ alkoxy-$C_1$ to $C_4$ alkyl) RNA, e.g., 2'-O-methoxyethyl RNA (MOE RNA).

Another suitable example of a modified ribonucleotide moiety is a ribonucleotide that has a methylene bridge between the 2'-oxygen atom and the 4'-carbon atom. See structure 5 in FIG. 1. An oligoribonucleotide molecule comprising ribonucleotide moieties that has a methylene bridge between the 2'-oxygen atom and the 4'-carbon atom is generally referred to as locked nucleic acid (LNA). See, for example, Kurreck et al., *Nucleic Acids Res.* 30, 1911-1918 (2002); Elayadi et al., Curr. Opinion Invest. Drugs 2, 558-561 (2001); Ørum et al., Curr. Opinion Mol. Ther. 3, 239-243 (2001); Koshkin et al., Tetrahedron 54, 3607-3630 (1998); Obika et al., *Tetrahedron Lett.* 39, 5401-5404 (1998). Locked nucleic acids are commercially available from Proligo (Paris, France and Boulder, Colo., USA).

Another suitable example of a modified ribonucleotide moiety is a ribonucleotide that is substituted at the 2' position with fluoro group. Such 2'-fluororibonucleotide moieties are known in the art. Molecules comprising 2'-fluororibonucleotide moieties are generally referred to herein as 2'-fluororibo nucleic acids (FANA). See structure 7 in FIG. 1. Damha et al., J. Am. Chem. Soc. 120, 12976-12977 (1998).

In another embodiment, the DNA virus microRNA molecule comprises at least one base bonded to an amino acid residue. Moieties that have at least one base bonded to an amino acid residue will be referred to herein as peptide nucleic acid (PNA) moieties. Such moieties are nuclease resistance, and are known in the art. Molecules having PNA moieties are generally referred to as peptide nucleic acids. See structure 6 in FIG. 1. Nielson, Methods Enzymol. 313, 156-164 (1999); Elayadi, et al, id.; Braasch et al., Biochemistry 41, 4503-4509 (2002), Nielsen et al., *Science* 254, 1497-1500 (1991).

The amino acids can be any amino acid, including natural or non-natural amino acids. Naturally occurring amino acids include, for example, the twenty most common amino acids normally found in proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val).

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenylacetic acid, and γ-phenyl-β-aminobutyric acid.

Non-naturally occurring amino acids also include derivatives of naturally occurring amino acids. The derivative of a naturally occurring amino acid may, for example, include the addition or one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include hydroxyl, $C_1$-$C_4$ alkoxy, amino, methylamino, dimethylamino, nitro, halo (i.e., fluoro, chloro, bromo, or iodo), or branched or unbranched $C_1$-$C_4$ alkyl, such as methyl, ethyl, n-propyl, isopropyl, butyl, isobutyl, or t-butyl.

Other examples of non-naturally occurring amino acids which are derivatives of naturally occurring amino acids include norvaline (Nva), norleucine (Nle), and hydroxyproline (Hyp).

The amino acids can be identical or different from one another. Bases are attached to the amino acid unit by molecular linkages. Examples of linkages are methylene carbonyl, ethylene carbonyl and ethyl linkages. (Nielsen et al., *Peptide Nucleic Acids-Protocols and Applications*, Horizon Scientific Press, pages 1-19; Nielsen et al., *Science* 254: 1497-1500.) One example of an amino acid residue of a PNA moiety is N-(2-aminoethyl)-glycine.

Figure 5:
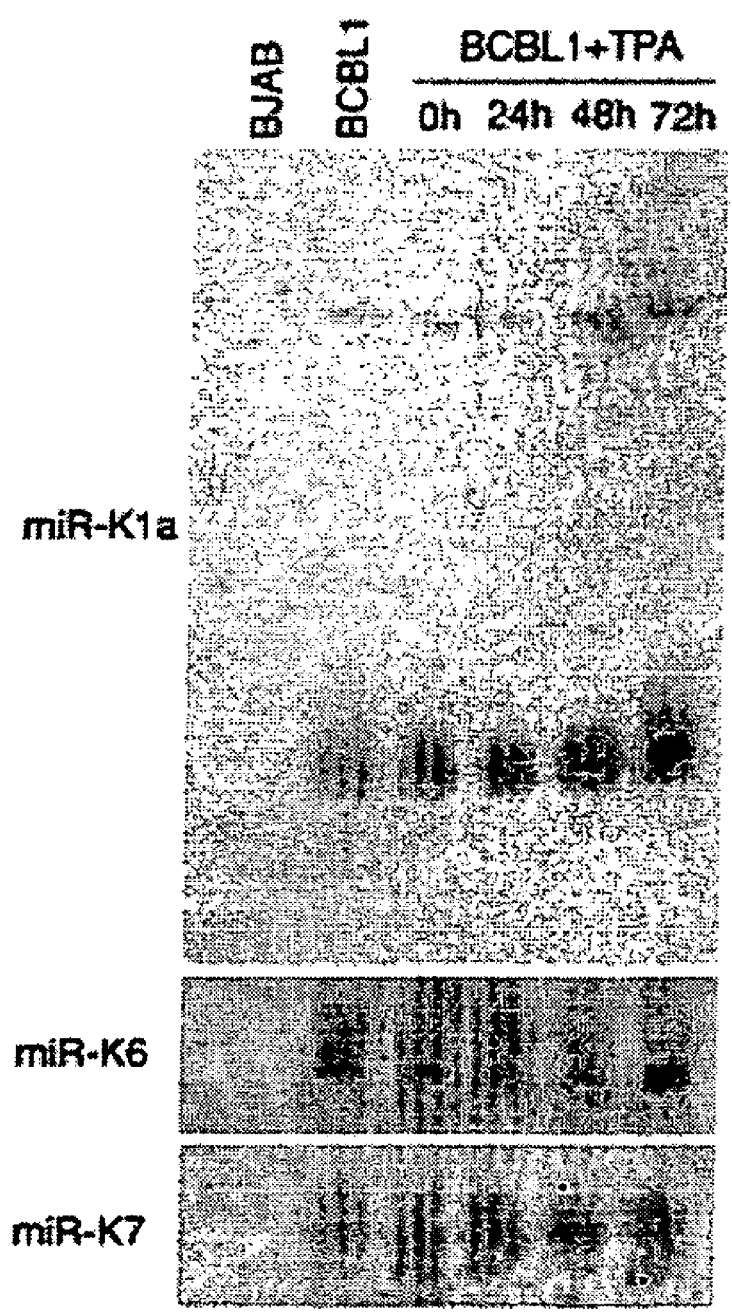
FIG. 5. KSHV mRNAs are differentially regulated upon induction of the lytic cycle. Northern blots for KSHV miR-K1a, miR-K6 and miR-K7 made from total RNA isolated from a KSHV negative (BJAB) cell line and from BCBL1 cells at 24 h, 48 h and 72 h after TPA treatment.

Further examples of PNA moieties include cyclohexyl PNA, retro-inverso PNA, phosphone PNA, propionyl PNA and aminoproline PNA. For a description of these PNA moieties, see FIG. 5 of Nielsen et al., *Peptide Nucleic Acids-Protocols and Applications*, Horizon Scientific Press, pages 1-19. FIG. 5 on page 7 of Nielsen et al. is hereby incorporated by reference.

PNA can be chemically synthesized by methods known in the art, e.g. by modified Fmoc or tBoc peptide synthesis protocols. The PNA has many desirable properties, including high melting temperatures (Tm), high base-pairing specificity with nucleic acid and an uncharged molecular backbone. Additionally, the PNA does not confer RNase H sensitivity on the target RNA, and generally has good metabolic stability.

Peptide nucleic acids are also commercially available from Applied Biosystems (Foster City, Calif., USA).

Additional nuclease resistant moieties are known in the art. For example, the DNA virus microRNA molecule comprises at least one morpholino phosphoroamidate nucleotide moiety. Molecules comprising morpholino phosphoroamidate nucleotide moieties are generally referred to as morpholino (MF) nucleic acids. See structure 8 in FIG. 1. Heasman, Dev. Biol. 243, 209-214 (2002). Morpholino oligonucleotides are commercially available from Gene Tools LLC (Corvallis, Oreg., USA).

In another example of a nuclease resistant moiety, the DNA virus microRNA molecule comprises at least one cyclohexene nucleotide moiety. Molecules comprising cyclohexene nucleotide moieties are generally referred to as cyclohexene nucleic acids (CeNA). See structure 10 in FIG. 1. Wang et al., J. Am. Chem. Soc. 122, 8595-8602 (2000), Verbeure et al., Nucleic Acids Res. 29, 4941-4947 (2001).

In a final example of a nuclease resistant moiety, the DNA virus microRNA molecule comprises at least one tricyclo nucleotide moiety. Molecules comprising tricyclo nucleotide moieties are generally referred to as tricyclo nucleic acids (tcDNA). See structure 9 in FIG. 1. Steffens et al., J. Am. Chem. Soc. 119, 11548-11549 (1997), Renneberg et al., J. Am. Chem. Soc. 124, 5993-6002 (2002).

In another embodiment, caps can be attached to one end, both ends, and/or between the ends of the molecule in order to increase nuclease resistance of the DNA virus microRNA analogs or unmodified isolated nucleic acid microRNA molecules of the present invention described above to exonucleoses. Any cap known to those in the art for increasing nuclease resistance can be employed.

Examples of such caps include inverted nucleotide caps and chemical caps. Inverted nucleotide caps can be attached at the 5' and/or 3' end. Chemical caps can be attached to one end, both ends, and/or between the ends of the molecule.

An inverted nucleotide cap refers to a 3'→5' sequence of nucleic acids attached to the DNA virus microRNA molecule or isolated nucleic acid microRNA molecules. There is no limit to the maximum number of nucleotides in the inverted cap just as long as it does not interfere with binding of the molecule to its target mRNA. Any nucleotide can be used in the inverted nucleotide cap. Usually, the nucleotide cap is less than about forty nucleotides in length, preferably less than about thirty nucleotides in length, more preferably less than about twenty nucleotides in length, and even more preferably less than about ten nucleotides in length. Typically, the inverted nucleotide cap is one nucleotide in length. The nucleotide for the inverted cap is generally thymine, but can be any nucleotide such as adenine, guanine, uracil, or cytosine.

A chemical cap refers to any chemical group known to those in the art for increasing nuclease resistance of nucleic acids. Example of such chemical caps include hydroxyalkyl groups (alkyl hydroxides) or aminoalkyl groups (alkyl amines). Hydroxyalkyl groups are sometimes referred to as alkyl glycoyl groups (e.g., ethylene glycol). Aminoalkyl groups are sometimes referred to as amino linkers.

The alkyl chain in the hydroxyalkyl group or aminoalkyl group can be a straight chain or branched chain. The minimum number of carbon atoms present in the alkyl chain is one, preferably at least two, and more preferably at least about three carbon atoms.

The maximum number of carbon atoms present in the alkyl chain is about eighteen, preferably about sixteen, and more preferably about twelve. Typical alkyl groups include methyl, ethyl, and propyl. The alkyl groups can be further substituted with one or more hydroxyl and/or amino groups.

Some examples of amino linkers are shown in Table C. The amino linkers listed in Table C lists are commercially available from TriLink Biotechnologies, San Diego, Calif.

TABLE C

Amino Linkers from TriLink Biotechnologies

2'-Deoxycytidine-5-C6 Amino Linker (3' Terminus)
2'-Deoxycytidine-5-C6 Amino Linker (5' or Internal)
3' C3 Amino Linker

TABLE C-continued

Amino Linkers from TriLink Biotechnologies

3' C6 Amino Linker
3' C7 Amino Linker
5' C12 Amino Linker
5' C3 Amino Linker
5' C6 Amino Linker
C7 Internal Amino Linker
Thymidine-5-C2 Amino Linker (5' or Internal)
Thymidine-5-C6 Amino Linker (3' Terminus)
Thymidine-5-C6 Amino Linker (Internal)

Chimeric DNA virus microRNA molecules containing a mixture of any of the moieties mentioned above are also known, and may be made by methods known, in the art. See, for example, references cited above, and Wang et al, Proc. Natl. Acad. Sci. USA 96, 13989-13994 (1999), Liang et al., Eur. J. Biochem. 269, 5753-5758 (2002), Lok et al., Biochemistry 41, 3457-3467 (2002), and Damha et al., J. Am. Chem. Soc. 120, 12976-12977 (2002).

The DNA virus microRNA molecules of the invention comprise at least ten, preferably at least thirteen, more preferably at least fifteen, and even more preferably at least twenty contiguous bases having the sequence of a naturally occurring DNA virus microRNA molecule. In a preferred embodiment, the DNA virus microRNA molecules comprise the entire sequence of a DNA virus microRNA molecule, such as any one of the DNA virus microRNA molecule sequences shown in Table A, Table A1 or Table A2.

The remaining bases in the molecule, if any, can be any modified or unmodified moiety described above. In one embodiment, the DNA virus microRNA molecule comprises at least one moiety which is a ribonucleotide moiety or a deoxyribonucleotide moiety.

Any number of additional moieties, up to a maximum of forty moieties, having any base sequence can be added to the moieties comprising the contiguous base sequence, as long as the total number of moieties in the molecule does not exceed fifty. The additional moieties can be added to the 5' end, the 3' end, or to both ends of the contiguous sequence. The additional bases can include a sequence of bases at the 5' end and/or a sequence of bases at the 3' end present in the hairpin precursor from which the DNA virus microRNA is derived. In one embodiment, the hairpin precursor sequence is any one of the hairpin precursor sequences shown in Table A, Table A1 or Table A2 or any fragment thereof.

For the contiguous bases mentioned above, up to thirty percent of the base pairs may be substituted by wobble base pairs. As used herein, wobble base pairs refer to either: i) substitution of a cytosine with a uracil, or 2) the substitution of an adenine with a guanine, in the sequence of the DNA virus microRNA molecule. These wobble base pairs are generally referred to as UG or GU wobbles. Table D shows the number of contiguous bases and the maximum number of wobble base pairs in the DNA virus microRNA molecule.

TABLE D

Number of contiguous Bases and Maximum Number of Wobble Bases

| | No. of Contiguous Bases | | | | | | | | | | | | |
|---|---|---|---|---|---|---|---|---|---|---|---|---|---|
| | 10 | 11 | 12 | 13 | 14 | 15 | 16 | 17 | 18 | 19 | 20 | 21 | 22 | 23 |
| Max. No. of Wobble Base Pairs | 3 | 3 | 3 | 3 | 4 | 4 | 4 | 5 | 5 | 5 | 6 | 6 | 6 | 6 |

Further, in addition to the wobble base pairs, up to ten percent, and preferably up to five percent of the contiguous bases can be additions, deletions, mismatches or combinations thereof. Additions refer to the insertion in the contiguous sequence of any moiety described above comprising any one of the bases described above. Deletions refer to the removal of any moiety present in the contiguous sequence. Mismatches refer to the substitution of one of the moieties comprising a base in the contiguous sequence with any of the above described moieties comprising a different base.

The additions, deletions or mismatches can occur anywhere in the contiguous sequence, for example, at either end of the contiguous sequence or within the contiguous sequence of the DNA virus microRNA molecule. Typically, the additions, deletions or mismatches occur at the end of the contiguous sequence if the contiguous sequence is relatively short, such as, for example, from about ten to about fifteen moieties in length. If the contiguous sequence is relatively long, such as, for example, a minimum of sixteen contiguous sequences, the additions, deletions, or mismatches typically occur anywhere in the contiguous sequence.

For example, none or one of the contiguous bases may be additions, deletions, or mismatches when the number of contiguous bases is ten to nineteen; and a maximum of one or two additions, deletions, or mismatches are permissible when the number of contiguous bases is twenty to twenty-three.

Furthermore, no more than fifty percent, and preferably no more than thirty percent, of the contiguous moieties contain deoxyribonucleotide backbone units. Table E and F show the number of contiguous bases and the maximum number of deoxyribonucleotide backbone units.

TABLE E

Fifty Percent of the Contiguous Moieties containing Deoxyribonucleotide Backbone Units

| | No. of Contiguous Bases | | | | | | | | | | | | | |
|---|---|---|---|---|---|---|---|---|---|---|---|---|---|---|
| | 10 | 11 | 12 | 13 | 14 | 15 | 16 | 17 | 18 | 19 | 20 | 21 | 22 | 23 |
| Max. No. of Deoxyribonucleotide Backbone Units | 5 | 5 | 6 | 6 | 7 | 7 | 8 | 8 | 9 | 9 | 10 | 10 | 11 | 11 |

TABLE F

Thirty Percent of the Contiguous Moieties Containing Deoxyribonucleotide Backbone Units

| | No. of Contiguous Bases | | | | | | | | | | | | |
|---|---|---|---|---|---|---|---|---|---|---|---|---|---|
| | 10 | 11 | 12 | 13 | 14 | 15 | 16 | 17 | 18 | 19 | 20 | 21 | 22 | 23 |
| Max. No. of Deoxyribonucleotide Backbone Units | 3 | 3 | 3 | 3 | 4 | 4 | 4 | 5 | 5 | 5 | 6 | 6 | 6 | 6 |

In another embodiment, in addition to the wobble base pairs and the further additions, deletions, and mismatches, described above, the moiety corresponding to position 11 in a naturally occurring DNA virus microRNA sequence can be an addition, deletion or mismatch.

Isolated MicroRNP

In another aspect, the invention provides an isolated microRNP comprising any of the isolated nucleic acid sequences described above or analogs of the DNA virus microRNAs described above.

Anti-DNA Virus MicroRNA Molecules

In another aspect, the invention provides an anti-DNA virus microRNA molecule. The anti-DNA virus microRNA molecule may be any of the isolated nucleic acid sequences described above or analogs of the DNA virus microRNAs described above, except that the sequence of bases of the anti-DNA virus microRNA molecule is complementary to the sequence of bases in an isolated nucleic acid DNA microRNA sequence or analogs of DNA virus microRNA molecules.

Examples of sequences of anti-DNA virus microRNA molecules is shown in Tables G, G1 and G2.

TABLE G

EBV anti-microRNA Sequences

| Virus | Anti-microRNA Sequence 5' → 3' |
|---|---|
| EBV | AACUCCGGGGCUGAUCAGGUUA (SEQ. ID. NO. 11) |
| | UUCAAUUUCUGCCGCAAAAGAUA (SEQ. ID. NO. 12) |
| | GUGUGCUUACACACUUCCCGUUA (SEQ. ID. NO. 13) |
| | AGCACGUCACUUCCACUAAGA (SEQ. ID. NO. 14) |
| | GCAAGGGCGAAUGCAGAAAAUA (SEQ. ID. NO. 15) |

TABLE G1

KSHV 8 anti-microRNA Sequences

| Virus | Anti-microRNA Sequence 5' → 3' |
|---|---|
| KSHV | GCCACUCGGGGGACAACACUA (SEQ. ID. NO. 48) |
| | GCCACUCGGGGGACAACACCA (SEQ. ID. NO. 49) |
| | AGCGGGGUUUACGCAGCUGGGU (SEQ. ID. NO. 50) |

TABLE G1-continued

KSHV 8 anti-microRNA Sequences

| Virus | Anti-microRNA Sequence 5' → 3' |
|---|---|
| | UUACGCAGCUGCGUAUACCCAG (SEQ. ID. NO. 51) |
| | CCGAUGGAUUAGGUGCUGCUGG (SEQ. ID. NO. 52) |
| | CUCAACAGCCCGAAAACCAUCA (SEQ. ID. NO. 53) |
| | CCGGCAAGUUCCAGGCAUCCUA (SEQ. ID. NO. 54) |
| | CCUAGAGUACUGCGGUUUAGCU (SEQ. ID. NO. 55) |
| | UCAGCUAGGCCUCAGUAUUCUA (SEQ. ID. NO. 56) |
| | CGCUGCCGUCCUCAGAAUGUGA (SEQ. ID. NO. 57) |
| | GUGUCACAUUCUGUGACCGCGA (SEQ. ID. NO. 58) |
| | CUUACACCCAGUUUCCUGUAAU (SEQ. ID. NO. 59) |
| | GAGCGCCAGCAACAUGGGAUCA (SEQ. ID. NO. 60) |
| | UCGGACACAGGCUAAGCAUUAA (SEQ. ID. NO. 61) |
| | CGUGCUCUCUCAGUCGCGCCUA (SEQ. ID. NO. 62) |

TABLE G2

HCMV anti-microRNA Sequences

| Virus | Anti-microRNA Sequence 5' → 3' |
|---|---|
| HCMV | ACUCUCACGGGAAGGCUAGUUA (SEQ. ID. NO. 90) |
| | CUACAAACUAGCAUUGUGGUGA (SEQ. ID. NO. 91) |
| | UCUUUCCAGGUGUCUUCAACGA (SEQ. ID. NO. 92) |
| | AGCCUGGAUCUCACCGUCACUU (SEQ. ID. NO. 93) |

TABLE G2-continued

HCMV anti-microRNA Sequences

| Virus | Anti-microRNA Sequence 5' → 3' |
|---|---|
| | GCGGUGAAGAAGGGGAGGACGA (SEQ. ID. NO. 94) |
| | AACGCUCUCGUCAGGCUUGUCA (SEQ. ID. NO. 95) |
| | GACAUCGUCACACCUAUCAUAA (SEQ. ID. NO. 96) |
| | CGGUCCGAGCCACUGAGCGGUU (SEQ. ID. NO. 97) |
| | UCAUCCACCUGAACAGACCGCU (SEQ. ID. NO. 98) |
| | CGCGGGAGCUGUCCAAGUGGAU (SEQ. ID. NO. 99) |
| | CGCCCACGGUGCGGGCAGAAUC (SEQ. ID. NO. 100) |

The anti-DNA virus microRNA molecule can be modified as described above for DNA virus microRNA molecules. In one embodiment, the contiguous moieties in the anti-DNA virus microRNA molecule are complementary to the corresponding DNA virus microRNA molecule. The degree of complementarity of the anti-DNA virus microRNA molecules are subject to the restrictions described above for analogs of DNA virus microRNA molecules, including the restriction relating to wobble base pairs, as well as those relating to additions, deletions and mismatches.

In a preferable embodiment, if the anti-DNA virus microRNA molecule comprises only unmodified moieties, then the anti-DNA virus microRNA molecule comprises at least one base, in the at least ten contiguous bases, which is non-complementary to the DNA virus microRNA and/or comprise a chemical cap.

In another preferable embodiment, if the at least ten contiguous bases in an anti-DNA virus microRNA molecule is perfectly complementary (i.e., 100%) to a DNA virus microRNA molecule, then the anti-DNA virus microRNA molecule contains at least one modified moiety in the at least ten contiguous bases and/or comprises a chemical cap.

In yet another embodiment, the moiety in the anti-DNA virus microRNA molecule at the position corresponding to position 11 of a naturally occurring DNA virus microRNA is non-complementary. The moiety in the anti-DNA virus microRNA molecule corresponding to position 11 of a naturally occurring DNA virus microRNA can be rendered non-complementary by any means described above, including by the introduction of an addition, deletion or mismatch, as described above.

Isolated

The nucleic acid molecule, DNA virus microRNA molecule or anti-DNA virus microRNA molecule is preferably isolated, which means that it is essentially free of other nucleic acids. Essentially free from other nucleic acids means that the nucleic acid molecule, DNA virus microRNA molecule or anti-DNA virus microRNA molecule is at least about 90%, preferably at least about 95% and, more preferably at least about 98% free of other nucleic acids.

Preferably, the molecule is essentially pure, which means that the molecule is free not only of other nucleic acids, but also of other materials used in the synthesis and isolation of the molecule. Materials used in synthesis include, for example, enzymes. Materials used in isolation include, for example, gels, such as SDS-PAGE. The molecule is at least about 90% free, preferably at least about 95% free and, more preferably at least about 98% free of other nucleic acids and such other materials.

Utility

The DNA virus microRNA molecules and anti-DNA virus microRNA molecules of the present invention have numerous in vitro, ex vivo, and in vivo applications.

For example, the microRNA molecules and/or anti-microRNA molecules of the present invention can be introduced into a cell to study the function of the microRNA. Any DNA viral microRNA molecule and/or anti-DNA viral microRNA molecule mentioned above can be introduced into a cell for studying their function.

In one embodiment, a microRNA in a cell is inhibited with a suitable anti-microRNA molecule. Alternatively, the activity of a microRNA molecule in a cell can be enhanced by introducing into the cell an additional microRNA molecule. The function of the microRNA can be inferred by observing changes associated with inhibition and/or enhanced activity of the microRNA in the cell.

Thus, in one aspect of the invention, the invention relates to a method for inhibiting microRNP activity in a cell. The microRNP comprises a DNA virus microRNA molecule. The microRNA molecule comprises a sequence of bases complementary to the sequence of bases in a single stranded anti-DNA virus microRNA molecule. Any anti-DNA virus microRNA molecule can be used in the method for inhibiting microRNP activity in a cell, as long as the anti-DNA virus microRNA is complementary, subject to the restrictions described above, to the DNA virus microRNA present in the microRNP.

The anti-DNA virus microRNA molecules of the present invention are capable of inhibiting microRNP activity by binding to the DNA virus microRNA in the microRNP in a host cell. MicroRNP activity refers to the cleavage or the repression of translation of the target sequence. The target sequence may be any sequence which is partially or perfectly complementary to the sequence of bases in a DNA virus microRNA. The target sequence can be, for example, a viral or host messenger RNA.

For example, a DNA virus can produce a microRNA which is complementary to a host derived target sequence that is beneficial to the host cell for defending against the viral infection. The DNA virus microRNA, which is packaged in a microRNP, will inhibit the beneficial effect of the target sequence. Accordingly, the introduction of the anti-DNA virus microRNA molecule inhibits the RNP activity, and thereby reduces harm from the virus.

Alternatively, a host cell can defend against a viral infection by transcribing a gene which is harmful to the virus. For instance, the gene may induce the cell to undergo apoptosis, and therefore the gene is harmful to the virus. A DNA virus microRNA complementary to the target sequence transcribed by the host cell is beneficial to the virus, because the DNA virus micro RNA (in a microRNP) will inhibit the ability of the host cell to undergo apoptosis. Accordingly, the introduction of DNA virus microRNA molecules promotes survival of the cell, thereby enhancing the infection.

The method for inhibiting microRNP activity in a cell comprises introducing into the cell a single-stranded anti-DNA virus microRNA molecule. The anti-DNA virus microRNA molecule can be introduced into a cell by any method described in the art. Some examples are described below.

The cell can be any cell capable of being infected with a particular DNA virus. Particular cells infected by a particular DNA virus are well known to those skilled in the art. For example, it is well known to those in the art that EBV preferentially infects B lymphocytes.

The microRNA molecules or anti-microRNA molecules can be introduced into a cell by any method known to those skilled in the art. For example, the molecules can be injected directly into a cell, such as by microinjection. Alternatively, the molecules can be contacted with a cell, preferably aided by a delivery system.

Useful delivery systems include, for example, liposomes and charged lipids. Liposomes typically encapsulate oligonucleotide molecules within their aqueous center. Charged lipids generally form lipid-oligonucleotide molecule complexes as a result of opposing charges.

These liposomes-oligonucleotide molecule complexes or lipid-oligonucleotide molecule complexes are usually internalized in cells by endocytosis. The liposomes or charged lipids generally comprise helper lipids which disrupt the endosomal membrane and release the oligonucleotide molecules.

Other methods for introducing a microRNA molecule or an anti-microRNA into a cell include use of delivery vehicles, such as dendrimers, biodegradable polymers, polymers of amino acids, polymers of sugars, and oligonucleotide-binding nanoparticles. In addition, pluoronic gel as a depot reservoir can be used to deliver the anti-microRNA oligonucleotide molecules over a prolonged period. The above methods are described in, for example, Hughes et al., Drug Discovery Today 6, 303-315 (2001); Liang et al. Eur. J. Biochem. 269 5753-5758 (2002); and Becker et al., In *Antisense Technology in the Central Nervous System* (Leslie, R. A., Hunter, A. J. & Robertson, H. A., eds), pp. 147-157, Oxford University Press.

Targeting of a microRNA molecule or an anti-microRNA molecule to a particular cell can be performed by any method known to those skilled in the art. For example, the microRNA molecule or anti-microRNA molecule can be conjugated to an antibody or ligand specifically recognized by receptors on the cell. For example, if the cell is a B lymphocyte, the antibody can be against the cell receptor CD19, CD20, CD21, CD23 or a ligand to these receptors.

In another embodiment, the invention provides a method for treating a DNA virus infection is a mammal in need thereof. The method comprises introducing into the mammal an anti-DNA virus microRNA molecule. The anti-DNA virus microRNA molecules can be introduced into the mammal by any method known to those in the art. For example, the above described methods for introducing the anti-DNA molecules into a cell can also be used for introducing the molecules into a mammal.

EXAMPLES

Example 1

Materials and Methods

Cell lines and viruses. The EBV negative BL-41 and EBV positive BL41/95 cells were described previously (Torsteinsdottir et al., *Int. J. Cancer* 1989, 43:273) and were maintained in RPMI 1640 (Gibco) supplemented with 10% FBS. BL41/95 but not BL-41 contained EBV, as confirmed by Western blot analysis using antibodies against EBNA-1. For analysis of EBV miRNA expression, we also cultured Hodgkin's lymphoma (HD) cells L540 and HD-MY-Z (EBV negative) and RPMI 6666 (EBV positive) and the Burkitt's lymphoma (BL) cells Ramos (EBV negative), Ous and Mutu (EBV positive), and EBV positive Marmoset B95-8 cells that produce infectious B95-8 viral particles. These cell lines were also maintained in RPMI 1640 (Gibco) supplemented with 10% FBS. The KSHV positive BCBL1 cell line was described previously (Renne et al. *Nat. Med.* 1996, 2:342-346) and was maintained in RPMI 1640 (Gibco) supplemented with 10% FBS. For the KSHV studies, to induce viral replication, a total of $5 \times 10^6$ BCBL1 cells were induced with 20 ng of phorbol-12-tetradecanoate-13-acetate (TPA)/ml and RNA was isolated 24, 48 and 72 h after TPA treatment. Primary human foreskin fibroblasts were cultured in MEM (GIBCO) supplemented with 10% FCS, 10 U/ml moronal, and 10 µg/ml neomycin sulphate. Cells at 90% confluency were infected with HCMV strain VR1814 at 5 PFU/cell and harvested when a strong cytopathic effect was visible, usually at about 4-5 days post-infection.

RNA preparation, cloning procedure and Northern blot analysis. Total RNA extraction was performed as described previously (Lagos-Quintana et al., *Curr. Biol.* 2002, 12:735). RNA size fractionation and cloning procedure have also been described. Northern blot analysis was performed as described (Lagos-Quintana et al., *Curr. Biol.* 2002, 12:735) loading 30 µg or 15 µg of total RNA per lane and using 5' $^{32}$P-radiolableled oligodeoxynucleotides complementary to the miRNA sequence. For the EBV studies, equal loading of the gels was confirmed by ethidium bromide staining of the tRNA band or by reprobing the blot for U6 snRNA using $^{32}$P-labeled 5'GCAGGGGCCATGCTAATCTTCTCTGTATCG SEQ. ID. NO. 16 oligodeoxynucleotide. Blots were stripped and reprobed several times. Complete stripping of the blot was confirmed by phosphorimaging of the membrane before reprobing.

DNA Sequencing of small RNA cDNA libraries. Bacterial colonies were picked into 96 well plates filled with 20 µl sterile water per well, then diluted 1:1 into a second 96 well plate containing 10 µl PCR cocktail (2 µl 10× Sigma JumpStart PCR buffer, 2 µl 2 mM deoxynucleoside triphosphate mixture, 0.4 µl each 10 µM M13 universal and reverse primers, 0.35 µl 1 U/µl JumpStart REDAccuTaq DNA polymerase (Sigma), and 4.85 µl water. The PCR cycling program consisted of 1'30" at 94° C., followed by 30 cycles of 94° C., 30"; 57° C., 30"; 72° C., 3'30", conditions which largely deplete the primers and deoxynucleotides, obviating the requirement for reaction cleanup prior to sequencing. After diluting the PCR products with 30 µl water, 3 µl was added to wells of a 96 well plate containing 17 µl sequencing cocktail consisting of 1 µl 2.5× BigDye Terminator v3.1 Cycle Sequencing Kit premix, 1.75 µl 5× buffer and 14.25 µl water, and sequencing reactions were carried out for 25 cycles (96° C., 10"; 50° C., 5"; 60° C., 4'). The reaction products were precipitated with 50 µl 100% ethanol/2 µl 3M NaOAc (pH 4.8), pellets were rinsed with 70% ethanol, and after the addition of 10 µL1

Hi-Di Formamide (Applied Biosystems) and denaturing at 94° C. for 10 min, samples were loaded onto an ABI 3730×l sequencer.

miRNA target prediction. We first obtained the 3' UTR sequences for 20,153 transcripts in the human genome using Ensmart (Kasprzyk et al., *Genome Res.* 2004, 14:160) as well as the sequences of 175 mature human mRNAs from the RFAM mRNA registry (Griffiths-Jones, *Nucleic Acids Res.*, 2004, 32:D109). miRanda (Enright et al., *Genome Biol.*, 2003, 5:RI, 1) was used to identify mRNA binding sequences in the 3' UTR sequences. The thresholds used for this scan were S:90 and .G: −17 kcal/mol. Targets that were in the 90th percentile of the raw alignment scores were selected as candidate mRNA targets.

Example 2

Identification of EBV Encoded microRNAs

We examined a large DNA virus of the Herpes family, Epstein barr virus (EBV) which preferentially infects human B cells. We cloned the small RNAs from a Burkitt's lymphoma cell line latently infected with EBV. Surprisingly, we found 4% of the cloned small RNAs originated from EBV (Tables 1 and 2).

TABLE 1

Composition of small RNA cDNA libraries prepared from non-infected (−) and DNA virus-infected human cell lines according to sequence annotation. The annotation was based on information from GenBank (http://www.ncbi.nih.gov/Genbank/index.html), a dataset of human tRNA sequences (http://rna.wustl.edu/GtRDB/Hs/Hs-seqs.html), a dataset of human and mouse sn/snoRNA sequences (http://mbcr.bcm.tmc.edu/smallRNA/Database), a database of microRNAs (http://www.sanger.ac.uk/Software/Rfam/microRNA/), predictions of microRNAs (35), and the repeat element annotation of the HG16 human genome assembly from UCSC (http://genome.cse.ucsc.edu). The total number of cloned sequences is indicated in parentheses at the bottom line of the table. Sequences that mapped to the human genome allowing up to two mismatches but could not be assigned a specific type were classified as Not annotated; those that did not match to the genome with more than 3 mismatches were classified as Not matched.

| | BL-41 Human Cell Line | |
|---|---|---|
| Type | — | EBV |
| rRNA | 37.00 | 41.92 |
| tRNA | 5.32 | 4.72 |
| microRNA | 44.36 | 33.94 |
| Repeat | 1.62 | 0.98 |
| Other ncRNA[a] | 4.33 | 5.80 |
| mRNA | 4.11 | 5.39 |
| Viral[b] | 0 | 4.15 |
| Not annotated | 2.26 | 2.23 |
| Not matched. | 0.99 | 0.88 |
| (No. seq.) | (2216) | (1930) |

[a]This includes snRNAs and snoRNAs and other known small cytoplasmic non-coding RNAs.
[b]The annotation for viral sequences is based on EBV B95-8 (GenBank V01555).

TABLE 2

Small RNA sequences derived from viral sequence. The position of the small RNA sequence is given relative to the viral genome sequences specified in Table 1 above.

| Virus | Small RNA Sequence 5' → 3' | Clones | Size range (nt) | Position, Orientation |
|---|---|---|---|---|
| EBV | UAACCUGAUCAGCCCCGGAGUU (SEQ. ID. NO. 1) | 2 | 21-22 | 53762-53783, + |
| | AAAUUCUGUUGCAGCAGAUAGC (SEQ. ID. NO. 17) | 3 | 22 | 55141-55162, + |
| | UAUCUUUUGCGGCAGAAAUUGAA (SEQ. ID. NO. 2) | 50 | 20-23 | 55176-55198, + |
| | UAACGGGAAGUGUGUAAGCACAC (SEQ. ID. NO. 3) | 23 | 19-23 | 55256-55278, + |
| | UCUUAGUGGAAGUGACGUGGU (SEQ. ID. NO. 4) | 1 | 21 | 151640-151660, + |
| | UAUUUUCUGCAUUCGCCCUUGC (SEQ. ID. NO. 5) | 2 | 22 | 153205-153226, + |

Most of the EBV sequences were cloned more than once and the analysis of the genomic sequence flanking the cloned RNAs suggested fold-back structures characteristic of microRNAs genes. The EBV microRNAs originated from 5 different dsRNA precursors that are clustered in two regions of the EBV genome (FIGS. 2A and B).

The EBV microRNAs were all readily detectable by Northern blotting, including the approximately 60-nt fold-back precursor for 3 of the 5 microRNAs (FIG. 2C). The first microRNA cluster is located within the mRNA of the BHFR1 gene encoding a distant Bcl-2 homolog, and we refer to these three microRNAs as miR-BHRF1-1 to miR-BHRF1-3.

miRBHFR1-1 is located in the 5' UTR and miR-BHRF1-2 and -3 are positioned in the 3' UTR of the BHRF1 mRNA. Structurally similar microRNA gene organization has been observed for some mammalian microRNAs that flank open reading frames in expressed sequence tags. The other EBV microRNAs cluster in intronic regions of the BART gene, and we refer to them as miR-BART1 and miR-BART2. Since microRNAs function in RNA silencing pathways either by targeting mRNAs for degradation or by repressing translation, we identified new viral regulators of host and/or viral gene expression.

Example 3

Predicated Target for Epstein Barr Virus Encoded microRNA

EBV latently infected cells can be found in three different latent stages (I to III, FIG. 2A) that are characterized by the expression of various subsets of the latent genes: six nuclear antigens (EBNAs 1, 2, 3A, B, C, and EBNA-LP), three latent membrane proteins (LMPs 1, 2A and 2B), two non-coding RNAs (EBERs 1 and 2) and transcripts from the BamHI A region (BARTs/CSTs) whose coding capacity is still controversial.

We isolated our small RNAs from a latent-stage-III EBV cell line that expresses all latent genes. In order to address if the expression of the EBV microRNAs is coupled with a specific latent stage, we probed for EBV microRNA expression in immortalized cell lines which are in different stages of latency, including Hodgkin's lymphoma (HD, latency II), Burkitt's lymphoma (BL) latency stage I cells, and virus-producing marmoset monkey lymphocytes B95-8 (latency III, with a fraction of 3 to 10% of cells expressing lytic stage antigens) (FIG. 2D).

BART microRNAs were detected in all latent stages consistent with the reported expression of BART during every stage of EBV infection. However, BART microRNA expression was elevated by about 10-fold in the virus producing marmoset cell line (FIG. 2D, lane 9, rows 5 and 6). Although several studies have attempted to identify proteins encoded from the different spliced transcripts of BART, the function of this region remains unknown. Our findings will help to assign a function to the BART region.

The expression pattern of BHRF1 microRNAs is dependent on the EBV latency stage. While cell lines in stage II and III expressed BHRF1 microRNAs (FIG. 2D, lanes 5-6), only one of the two stage I cell lines expressed BHRF1 microRNAs (FIG. 2D, lanes 7, 8). Latency I cell lines are thought to express only EBNA 1, the EBERs and the BARTs.

The expression of a transcript deriving from the BHRF1 region in one of the latency stage I cell lines as well as its expression in stage II cell lines, suggests a new latency stage I/II promoter upstream of the known latency stage I/II Qp promoter (FIG. 2A). A new subdivision of latency I stages may have to be introduced to distinguish between BHRF1 microRNA expressing cell lines in latency I.

Although BHRF1 protein is only detected in lytic stage, latent stage EBV transcripts encompassing the BHRF1 region were observed previously. It is likely that the microRNAs BHRF1-1 to 3 are also expressed during lytic stage along with the BHRF1 protein. The high-level transcription of BHRF1 during the lytic cycle may exceed the cellular microRNA processing capacity and unprocessed transcripts could then be translated.

To identify targets for EBV microRNAs, we used a computational method recently developed for prediction of Drosophila microRNAs targets (Enright et al., Genome Biol., 2003, 5:RI, 1). A set of approximately 20,000 non-redundant human 3' UTRs and the genome sequence of EBV were searched for potential microRNA binding sites. The top scoring hits for which a gene function annotation was available, are listed in Table 3. The majority of predicted host cell targets have more than one binding site for the viral microRNA, and approximately 50% of these are additionally targeted by one or several host cell microRNAs. Multiple microRNA binding sites are believed to act synergistically and increase targeting efficiency in a cooperative non-linear fashion.

TABLE 3

Predicted host cell target mRNAs of EBV microRNA. The gene name is indicated as recommended by HUGO, and the gene function annotation was extracted from Ensembl. The number of predicted microRNA binding sites in the 3' UTR of the target gene (NS) and a percentile score ranking the target site predictions (%-ile) are indicated. If human microRNAs are also predicted to bind to a putative EBV microRNA regulated target, it is indicated in the last column. The predicated human microRNA binding sites are also conserved in the orthologous mRNAs in mouse.

| EBV microRNA | Gene ID | Proposed function | NS | %-ile | Human miRNA |
|---|---|---|---|---|---|
| | | Apoptosis, cell proliferation | | | |
| BART1, BHRF1-2 | BCL2 | Apoptosis regulator Bcl-2 | 3, 1 | 100, 98 | miR-217, miR-140 |
| BHRF1-1 | P53 | Tumor suppressor P53 | 2 | 98 | |
| BHRF1-1 | E2F1 | Retinoblastoma Binding protein 3, Transcription factor E2F-1 | 2 | 98 | miR-20, miR-106 |
| | | Transcription regulation | | | |
| BART1 | HIC2 | Hypermethylated in Cancer 2 Protein | 2 | 99 | |
| BART1 | ZNF177 | Zinc Finger protein 177 | 4 | 100 | |
| BART2 | UBN1 | Ubinuclein 1 | 3 | 100 | |
| BHRF1-1 | CBFA2T2 | Myeloid Translocation gene-related protein 1 | 3 | 100 | miR-301 |
| BHRF1-3 | NSEP1 | Y Box Binding protein | 1 | 94 | miR-95, miR-216, miR-136 |

TABLE 3-continued

Predicted host cell target mRNAs of EBV microRNA. The gene name is indicated as recommended by HUGO, and the gene function annotation was extracted from Ensemble. The number of predicted microRNA binding sites in the 3' UTR of the target gene (NS) and a percentile score ranking the target site predictions (%-ile) are indicated. If human microRNAs are also predicted to bind to a putative EBV microRNA regulated target, it is indicated in the last column. The predicated human microRNA binding sites are also conserved in the orthologous mRNAs in mouse.

| EBV microRNA | Gene ID | Proposed function | NS | %-ile | Human miRNA |
|---|---|---|---|---|---|
| BHRF1-3, BART2 | TGIF | 5'-TG-3' Interacting factor, Homeobox protein TGIF | 1, 1 | 97 97 | miR-194 |
| | | Immune response | | | |
| BART2 | LRBA | Lipopolysaccharide-responsive and beige like protein, BCL8 Homolog | 4 | 99 | miR-15a, miR-146 miR-29a |
| BHRF1-1 | LILRB5 | Leukocyte immunoglobulin receptor, subfamily B, member 5 | 2 | 100 | |
| BHRF1-3 | PRF1 | Perforin 1 precursor | 1 | 99 | |
| | | Signal transduction | | | |
| BART1 | CXCL12 | Stromal cell derived factor 1 precursor, Pre-B growth Stimulating factor | 3 | 100 | miR-106, miR-135 miR-197 |
| BART2 | GAB2 | GRB2-Associated Binding Protein 2 | 4 | 100 | miR-155 |
| BART2 | TNFRSF1A | Tumor Necrosis Factor Receptor Superfamily member 1A | 2 | 99 | |
| BHRF1-2 | PIK3R1 | Phosphatidylinositol 3-kinase regulatory Alpha Subunit | 1 | 92 | let-7b |
| BHRF1-2, BART2 | B7RP-1 | B7 homolog, ICOS ligand precursor | 1, 3 | 97, 99 | miR-155 |
| BHRF1-3 | CXCL11 | Small inducible cytokine B11 precursor, I-TAC | 3 | 100 | |
| | | Chromosome organization | | | |
| BHRF1-2 | CENPA | Centromere Protein A | 1 | 98 | miR-16 |

Several of the predicted viral microRNA targets are prominent regulators of cell proliferation and apoptosis, which are presumably important for growth control of the infected cells. microRNA modulation of cell proliferation also provides new leads for studying the association of EBV with several cancerous malignancies. Another important group of EBV microRNA targets are B-cell specific chemokines and cytokines, which are important for leukocyte activation and/or chemotaxis. Down-regulation of these genes presumably contributes to escape of EBV-infected B cells from activated cytotoxic T cells. Additional targets include transcriptional regulators and components of signal transduction pathways that are critical for maintaining or switching between EBV lytic and latent stages.

Example 4

EBV Encoded microRNA miR-BART2 Targets Virally Encoded DNA Polymerase BALF5

One of the EBV-encoded microRNAs, miR-BART2, is capable of targeting the virally encoded DNA polymerase BALF5 for degradation (FIG. 3). miR-BART2 is transcribed anti-sense to the BALF5 transcript and is therefore perfectly complementary to the BALF5 3' UTR and able to subject this mRNA for degradation. Similarly, the clustered miRB-HRF1-2 and -3 are complementary to the transcript encoding the lytic gene BFLF2 (FIG. 2A), whose function is currently unknown. The down-regulation of lytic genes by viral microRNAs may contribute to establishment and maintenance of latent infection.

Example 5

Identification of KSHV Encoded microRNAs

The role of Kaposi's sarcoma-associated herpesvirus (KSHV) in various lymphomas is firmly established. To identify KSHV microRNAs, we cloned the small RNAs from a body cavity based lymphoma (BCBL) cell line, latently infected with KSHV. We found that up to 21% of the total cloned small RNAs (34% of the cloned cellular mRNAs), originated from KSHV (Tables 4 and 5).

TABLE 4

Composition in percentage of small RNA cDNA libraries prepared from KSHV-infected human cell line according to sequence annotation. The annotation was based on information from GenBank (http://www.ncbi.nih.gov/Genbank/index.html), a dataset of human tRNA sequences (http://rna.wustl.edu/GtRDB/Hs/Hs-seqs.html), a dataset of human and mouse sn/snoRNA sequences (http://mbcr.bcm.tmc.edu/smallRNA/Database), a database of miRNAs (http://www.sanger.ac.uk/Software/Rfam/mirna/), predictions of miRNAs, and the repeat element annotation of the HG16 human genome assembly from UCSC (http://genome.cse.ucsc.edu). The total number of cloned sequences is indicated in parentheses at the bottom line of the table. Sequences that mapped to the human genome allowing up to two mismatches but could not be assigned a specific type were classified as "Not annotated". The annotation for viral sequences is based on the published genomic sequence of KSHV BC-1 (GenBank U75698).

| Type | Composition of small RNAs cDNA library BCBL1 (%) |
|---|---|
| rRNA | 3.22 |
| tRNA | 4.78 |
| sn/sno-RNA | 0.29 |
| miscRNA | 2.14 |
| Repeat | 2.24 |
| mRNA | 1.75 |
| miRNA | 61.60 |
| Viral | 20.96 |
| Not annotated | 3.02 |
| (No. seq.) | (1026) |

TABLE 5

Small RNA sequences derived from KSHV.
The position of the small RNA sequence is
given relative to the viral genome sequence
specified in Table 4.

| Small RNA sequence (5' to 3') | No. Seq | Position, orientation |
|---|---|---|
| UAGUGUUGUCCCCCCGAGUGGC (SEQ. ID. NO. 18) | 36 | 117971-117991, - |
| UGGUGUUGUCCCCCCGAGUGGC (SEQ. ID. NO. 19) | 39 | 117971-117991, - |
| ACCCAGCUGCGUAAACCCCGCU (SEQ. ID. NO. 20) | 2 | 119338-119359, - |
| CUGGGUAUACGCAGCUGCGUAA (SEQ. ID. NO. 21) | 20 | 119304-119325, - |
| CCAGCAGCACCUAAUCCAUCGG (SEQ. ID. NO. 22) | 14 | 120796-120817, - |
| UGAUGGUUUUCGGGCUGUUGAG (SEQ. ID. NO. 23) | 9 | 120765-120786, - |
| UAGGAUGCCUGGAACUUGCCGGU (SEQ. ID. NO. 67) | 5 | 121266-121287, - |
| UAGAAUACUGAGGCCUAGCUGA (SEQ. ID. NO. 26) | 12 | 121417-121438, - |
| AGCUAAACCGCAGUACUCUAGG (SEQ. ID. NO. 25) | 34 | 121455-121476, - |
| UCGCGGUCACAGAAUGUGACA (SEQ. ID. NO. 63) | 12 | 121546-121566, - |
| UCACAUUCUGAGGACGGCAGCGA (SEQ. ID. NO. 64) | 2 | 121586-121608, - |
| AUUACAGGAAACUGGGUGUAAGC (SEQ. ID. NO. 65) | 12 | 121889-121910, - |
| UGAUCCCAUGUUGCUGGCGCU (SEQ. ID. NO. 66) | 13 | 120359-120380, - |
| UUAAUGCUUAGCCUGUGUCCGA (SEQ. ID. NO. 31) | 4 | 120580-120601, - |
| UAGGCGCGACUGAGAGAGCACG (SEQ. ID. NO. 32) | 1 | 119945-119966, - |

Figure 4A:
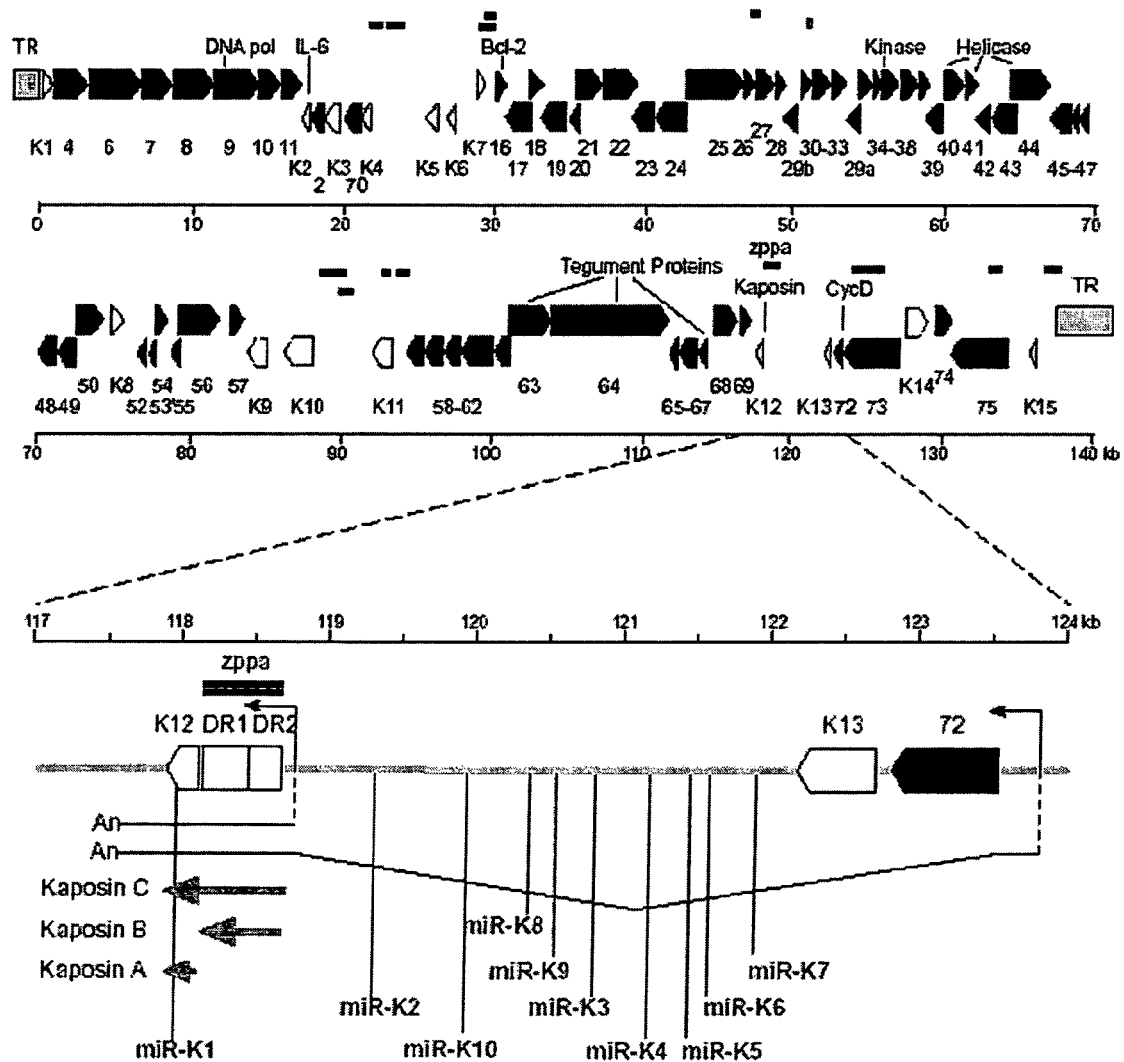
FIG. 4. Genomic positions and foldback structures of KSHV mRNAs. (A) Genomic positions of KSHV microRNAs. Solid arrows indicate open reading frames (ORF) conserved in Herpes Saimiri virus, open arrows indicate the unique KSHV ORFs. Repeat regions are shown as small filled rectangles above the ORFs. Cloned mRNAs are shown as dotted lines. The two possible promoters for K12 transcript are indicated as a black arrow, and K12 transcripts as a black lines, the intronic region in the larger transcript is depicted as a break in the line. The thick grey arrows show ORF for Kaposin proteins A, B and C. (B) Foldback precursors of KSHV microRNAs. The cloned mature microRNAs are highlighted in red.

Most of the KSHV sequences were cloned more than once and the analysis of the genomic sequence flanking the cloned RNAs suggested fold-back structures characteristic of microRNA genes. The KSHV microRNAs originated from 10 different dsRNA precursors that are all clustered in the same region of the KSHV genome (FIGS. 4A and 4B).

The KSHV microRNAs were designated miR-K1 to miR-K10. The cluster is located within the mRNA of the K12 gene encoding a protein named Kaposin, which possesses some oncogenic properties. Interestingly, miR-K1 is located within the coding sequence of K12. Previous reports suggest that the K12 coding sequence region is complex and encodes several proteins named Kaposin A, B, and C (see FIG. 4A).

We also identified two isoforms of miR-K1, i.e. miR-K1a and miR-K1b, which differ by one nucleotide at position 2 (see Table 6). MiR-K1a corresponds to the sequenced genome present in BCBL1 cells. MiR-K1b appears to be derived from a sequence isolated from a primary effusion lymphoma (PEL) tumor. Thus, two difference viral genomes or quasi-species may be present in the BCBL1 cell line. MiR-K2 to miR-K10 are located in the intronic region of a longer transcript encoding K12 whose promoter is located upstream of the ORF 72 (see FIG. 4A).

We next investigated whether KSHV mRNAs are differentially regulated upon induction of the lytic cycle. BCBL1 cells harbor replication competent KSHV. Upon treatment with TPA, these cells undergo the complete program of KSHV gene expression, resulting ultimately in viral replication and the release of mature virions.

We isolated total RNA after various times of TPA treatment and probed for KSHV mRNAs expression by Northern blot. Only miR-K1a expression was induced upon treatment, whereas mRNAs in the intronic regions, such as miR-K6 and miR-K7, where not affected (FIG. 5). This indicates that miR-K1a and miR-K2 to K10 may originate from different primary transcripts (FIG. 4A).

The identification of mRNAs in the genome of KSHV will provide new insights in the understanding of the oncogenic properties of the virus.

TABLE 6

KSHV miRNAs mature and precursor sequences. In bold the
mature form, underlined the non-functional star sequence
that was cloned for miR-K2 and miR-K6.

| KSHV miRNA | microRNA sequence (5' to 3') | Hairpin precursor sequence (5' to 3') |
|---|---|---|
| miR-K1a | UAGUGUUGUCCCCCCGAGUGGC (SEQ. ID. NO. 18) | CUGGAGGCUUGGGGCGAUACCACCACU CGUUUGUCUGUUGGCGAUUAGUGUUG UCCCCCCGAGUGGCCAG (SEQ. ID. NO. 33) |
| miR-K1b | UGGUGUUGUCCCCCCGAGUGGC (SEQ. ID. NO. 19) | CUGGAGGCUUGGGGCGAUACCACCACU CGUUUGUGUGUUGGCGAUUGGUGUUG UCCCCCCGAGUGGCCAG (SEQ. ID. NO. 34) |
| miR-K2 | * ACCCAGCUGCGUAAACCCCGCU (SEQ. ID. NO. 20) CUGGGUAUACGCAGCUGCGUAA (SEQ. ID. NO. 21) | GGGUCU<u>ACCCAGCUGCGUAAACCCCGC</u> UGCGUAAACACAGCUGGGUAUACGCA GCUGCGUAACCC (SEQ. ID. NO. 35) |

TABLE 6-continued

KSHV miRNAs mature and precursor sequences. In bold the
mature form, underlined the non-functional star sequence
that was cloned for miR-K2 and miR-K6.

| KSHV miRNA | microRNA sequence (5' to 3') | Hairpin precursor sequence (5' to 3') |
|---|---|---|
| miR-K3 | 5p CCAGCAGCACCUAAUCCAUCGG (SEQ. ID. NO. 22) 3p UGAUGGUUUUCGGGCUGUUGAG (SEQ. ID. NO. 23) | CUUGUCCAGCAGCACCUAAUCCAUCG GCGGUCGGGCUGAUGGUUUUCGGGCU GUUGAGCGAG (SEQ. ID. NO. 37) |
| miR-K4 | UAGGAUGCCUGGAACUUGGCGGU (SEQ. ID. NO. 67) | UGACCUAGGUAGUCCCUGGUGCCCUAA GGGUCUAGAUCAAGCAGUUAGGAUGC CUGGAACUUGCCGGUCA (SEQ. ID. NO. 39) |
| miR-K5 | 5p AGGUAAACCGCAGUACUCUAGG (SEQ. ID. NO. 25) 3p UAGAAUACUGAGGGCUAGCUGA (SEQ. ID. NO. 26) | AUAACUAGCUAAACCGCAGUACUCUA GGGCAUUGAUUUGUUAGAUAGAAUAC UGAGGCCUAGCUGAUUAU (SEQ. ID. NO. 40) |
| miR-K6 | UCACAUUCUGAGGACGGCAGCGA (SEQ. ID. NO. 64) * UGGCGGUCACAGAAUGUGAGA (SEQ. ID. NO. 63) | GGCUAUCACAUUCUGAGGACGGCAGC GACGUGUGUCUAACGUCAACG<u>UCGCG</u> <u>GUCACAGAAUGUGAC</u>ACC (SEQ. ID. NO. 42) |
| miR-K7 | AUUACAGGAAACUGGGUGUAAGC (SEQ. ID. NO. 65) | GGAUUACAGGAAACUGGGUGUAAGC UGUACAUAAUCGCCGGCAGGACCUGUU UCCUGCAAGCCUCGU (SEQ. ID. NO. 44) |
| miR-K8 | UGAUCCCAUGUUGCUGGCGCU (SEQ. ID. NO. 66) | GCGUUGAGCGCCACCGGACGGGGAUU UAUGCUGUAUCUUACUACCAUGAUCC CAUGUUGCUGGCGCUCACGG (SEQ. ID. NO. 45) |
| miR-K9 | UUAAUGCUUAGCCUGUGUCCGA (SEQ. ID. NO. 31) | CGCUUUGGUCACAGCUUAAACAUUUC UAGGGCGGUGUUAUGAUCCUUAAUGC UUAGCCUGUGUCCGAUGCG (SEQ. ID. NO. 46) |
| MiR-K10 | UAGGCGCGAGUGAGAGAGCACG (SEQ. ID. NO. 32) | CGCGCACUGGCUCACUAACGCCCCGCU UUUGUCUGUUGGAAGCAGCUAGGCGC GACUGAGAGAGCACGCG (SEQ. ID. NO. 47) |

Example 6

Identification of HCMV Encoded microRNAs

HCMV is a ubiquitous member of the β-herpesvirus family. Although HCMV infection of healthy children and adults is normally asymptomatic, it remains a leading cause of birth defects and an important cause of mortality in immunocompromised individuals.

Small RNAs were cloned from primary human foreskin fibroblasts lytically infected with HCMV clinical strain VR1814. We cloned 424 small RNAs deriving from the virus genome in HCMV infected cells. Of these, 171 sequences were cloned once, and were dispersed throughout the genome; the 253 remaining sequences were cloned multiple times and analysis of the genomic sequences flanking these suggested structures characteristic of mRNAs (Tables 7 and 8 and FIG. 6).

Four miRNAs were located in the UL region of the genome, and five derived from the US region. Interestingly, five mRNAs, miR-UL3, miR-UL4, miR-US3, miR-US4 and miR-US5 are transcribed on the complementary strand to known open reading frames (ORFs) (FIG. 6A). These five mRNAs may be involved in the cleavage of the complementary transcripts, as previously described for EBV miR-BART2 and the DNA polymerase BALF5. UL114 is a homolog of the mammalian uracyl-DNA glycosylase and has been shown to be required for efficient viral DNA replication.

UL150 is an ORF that is present in the clinical strains of HCMV, but not in the laboratory strains.

The other four mRNAs are either located in intergenic regions (miR-UL1, miR-US1 and miR-US2) or in an intronic region (miR-UL2). It is interesting to note that miR-UL2 is located in the intron of UL36, which has been described as an inhibitor of apoptosis that suppresses caspase-8 activation.

TABLE 7

Composition in percentage of
small RNA cDNA libraries prepared from HCMV-infected
human cell line according to sequence annotation (see Table 4).
The annotation for viral sequences is based on the published genomic
sequence of HCMV FIX-BAC isolate VR1814 (Genbank AC146907).

| Type | Fibroblasts HCMV (%) |
|---|---|
| rRNA + tRNA | 44.72 |
| Other ncRNA | 3.12 |
| mRNA | 4.51 |
| Repeat | 5.61 |
| miRNA | 20.41 |
| Viral | 17.88 |
| Not annotated | 3.75 |
| (No. seq.) | (2371) |

TABLE 8

HCMV miRNAs mature and precursor sequences
In bold the mature form, underlined the non-functional star sequence.

| HCMV miRNA | Mature sequence | Seq. No. | Hairpin precursor sequence | Position of the precursor, orientation‡ |
|---|---|---|---|---|
| miR-UL1 | UAACUAGCCUUCCCGUGAGA (SEQ. ID. NO. 101) | 101 | CCUGUCUAACUAGCCUUCCCGUGAGAGUUUAUG AACAUGUAUCUCACCAGAAUGCUAGUUUGUAGA GG (SEQ. ID. NO. 79) | 27644-27711, + |
| miR-UL1* | UGAGCAGAAUGCUAGUUUGUAG (SEQ. ID. NO. 69) | 11 | | |
| miR-UL2 | UCGUUGAAGACACCUGGAAAGA (SEQ. ID. NO. 70) | 9 | CCACGUCGUUGAAGACACCUGGAAAGAGGACGU UCGCUCGGGCACGUUCUUUCCAGGUGUUUUCAAC GUGCGUGG (SEQ. ID. NO. 81) | 49495-49569, + |
| miR-UL3 | AAGUGACGGUGAGAUGCAGGCU (SEQ. ID. NO. 71) | 22 | GACAGCCUCGGGAUCACAUGGUUACUCAGCGUCU GCCAGGGUAAGUGACGGUGAGAUCCAGGCUGUC (SEQ. ID. NO. 82) | 164118-164184, + |
| miR-UL4 | UCGUCCUCCCCUUCUUCACCG (SEQ. ID. NO. 102) | 5 | AGCAGGUGAGGUUGGGCGGACAACGUGUUGCG GAUUGUGGCGAGAACGUCGUCCUCCCCUUCUUC ACCGCC (SEQ. ID. NO. 83) | N.C.† |
| miR-US1 | UGACAAGCCUGACGAGAGCGU (SEQ. ID. NO. 103) | 4 | UGAACGCUUUCGUCGUGUUUUUCAUGCAGCUUU UACAGACCAUGACAAGCCUGACGAGAGCGUUCA (SEQ. ID. NO. 84) | |
| miR-US2 | UUAUGAUAGGUGUGACGAUGUC (SEQ. ID. NO. 74) | 46 | GGAGGCUUUCGCCACACCUAUCCUGAAAGCGUUG CAUUCUUUAUGAUAGGUGUGACGAUGUCUUU (SEQ. ID. NO. 85) | 197120-197184, + |
| miR-US3 | AACCGCUCAGUGGCUCGGACC (SEQ. ID. NO. 104) | 37 | UGUGAACCGCUCAGUGGCUCGGACCGCCGGCUG UUUGUGCGCACCGGUCCGAACGCUAGGUCGGUUC UCA (SEQ. ID. NO. 86) | 216177-216246, − |
| miR-US4-5p | AGCGGUCUGUUCAGGUGGAUGA (SEQ. ID. NO. 76) | 11 | CGGUUAGCGGUCUGUUCAGGUGGAUGAGGGCU CUUCACGGUCGGGCACUCGGCUGUGCCUGUCAUC CACUUGGAGAGCUCCCGCGGUCCG (SEQ. ID. NO. 87) | 216379-216468, − |
| miR-US4-3p | AUCCACUUGGAGAGCUCCCGCGG (SEQ. ID. NO. 105) | 3 | | |
| miR-US5 | GAUUGUGCCCGGACCGUGGGCG (SEQ. ID. NO. 78) | 4 | CACGGUUGAUUGUGCCCGGACCGUGGGCGCGA CGAAACCCACCGUCACGGUCCGAGCACAUCCAAA CGUG (SEQ. ID. NO. 89) | 221403-221472, − |

‡Positions are given relative to the laboratory strain AD169, which is fully annotated (Genbank NC_001347)
†miR-UL4 is the only HCMV miRNA that is not conserved between the FIX strain used here and the AD169 strain. It is located opposite to the gene ULI50, and the precursor location relative to the published HCMV FIX-BAC sequence (Genbank AC 146907) is 34630-34701 (−)

What we claim is:

1. An isolated nucleic acid human cytomegalovirus (HCMV) microRNA molecule having a maximum of 50 nucleotides comprising any one of SEQ ID NOS: 76 and 77.

2. A vector comprising an isolated nucleic acid molecule according to claim 1.

3. An isolated nucleic acid HCMV hairpin precursor microRNA molecule consisting of any one of SEQ ID NOS: 83 and 87.

4. A vector comprising an isolated nucleic acid molecule according to claim 3.

* * * * *